US009849195B2

(12) United States Patent
Davidson

(10) Patent No.: US 9,849,195 B2
(45) Date of Patent: Dec. 26, 2017

(54) METHODS AND COMPOSITIONS FOR TREATING BRAIN DISEASES

(75) Inventor: Beverly L. Davidson, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 165 days.

(21) Appl. No.: 14/008,994

(22) PCT Filed: Apr. 2, 2012

(86) PCT No.: PCT/US2012/031896
§ 371 (c)(1),
(2), (4) Date: Jul. 24, 2014

(87) PCT Pub. No.: WO2012/135857
PCT Pub. Date: Oct. 4, 2012

(65) Prior Publication Data
US 2014/0088179 A1    Mar. 27, 2014

Related U.S. Application Data

(60) Provisional application No. 61/470,460, filed on Mar. 31, 2011.

(51) Int. Cl.
*C12N 15/11*  (2006.01)
*A61K 48/00*  (2006.01)
*C12N 15/86*  (2006.01)
*C12N 9/48*  (2006.01)

(52) U.S. Cl.
CPC .......... *A61K 48/0075* (2013.01); *C12N 9/485* (2013.01); *C12N 15/86* (2013.01); *C12N 2799/025* (2013.01)

(58) Field of Classification Search
CPC ........................ C12N 15/1137; C12N 2310/14
See application file for complete search history.

(56) References Cited

U.S. PATENT DOCUMENTS

| | | | |
|---|---|---|---|
| 5,821,104 A | 10/1998 | Holm et al. | |
| 6,302,685 B1 | 10/2001 | Lobel et al. | |
| 6,468,524 B1 | 10/2002 | Chiorini et al. | |
| 6,855,314 B1 | 2/2005 | Chiorini et al. | |
| 8,110,556 B2 | 2/2012 | Lobel et al. | |
| 2002/0037867 A1 | 3/2002 | Wilson et al. | |
| 2005/0136036 A1* | 6/2005 | During ..................... | C12N 9/88 424/93.2 |
| 2005/0153906 A1 | 7/2005 | Bedwell et al. | |
| 2009/0162332 A1 | 6/2009 | Davidson et al. | |
| 2010/0173979 A1 | 7/2010 | Dodge et al. | |
| 2011/0038851 A1 | 2/2011 | Schlossmacher et al. | |
| 2011/0166074 A1 | 7/2011 | Maxfield | |

FOREIGN PATENT DOCUMENTS

| | | |
|---|---|---|
| WO | 2014089449 A1 | 6/2014 |
| WO | 2014184576 A2 | 11/2014 |

OTHER PUBLICATIONS

Li et al. Brain Research 1122, 2006, pp. 1-9.*
Hackett et al., "Safety of Direct Administration of AAV2chhCLN2, a Candidate Treatment for the Central Nervous System Manifestations of Late Infantile Neuronal Ceroid Lipofuscinosis, to the Brain of Rats and nonhuman Primates", *Gene Therapy* vol. 16 (12), 1484-1503 (2005).
Katz et al., "CSF-Mediated Distribution of TPP1 from AAV Transduced Brain Ependyma Promotes Widespread Enzyme Activity in Nonhuman Primate Brain and Improves CNS Phenotypes in LINCL Dogs", *Molecular Therapy*, vol. 19 (7), 1362 (2011).
Sands et al., "Gene Therapy for Lysosomal Storage Diseases", *Molecular Therapy* vol. 13 (5), 839-849 (2006).
Wang et al., "Recombinant AAV serotype 1 transduction efficiency and tropism in the murine brain", *Gene Therapy* 10, 1528-1534 (2003).
Watson et al., "Intrathecal administration of AAV vectors for the treatment of lysosomal storage in the brains of MPS I mice", *Gene Therapy* 13, 917-925 (2006).
Worgall et al., "Treatment of Late Infantile Neuronal Ceroid Lipofuscinosis by CNS Administration of a Serotype 2 Adeno-Associated Virus Expressing CLN2 cDNA", *Human Cene Therapy*, vol. 19 (5), 463-474 (2008).
Chang et al. "Intraventricular enzyme replacement improves disease phenotypes in a mouse model of late infantile neuronal ceroid lipofuscinosis," *Mol Ther*. 16(4), 649-656 (2008).
Chen et al., "Molecular signatures of disease brain endothelia provide new sites for CNS-directed enzyme therapy," Nature Medicine 15(1):1215-1219 (2009).
Crystal RG et al., "Clinical protocol. Administration of a replicationdeficient adeno-associated virus gene transfer vector expressing the human CLN2 cDNA to the brain of children with late infantile neuronal ceroid lipofuscinosis", *Hum Gene Ther*. 15(11), 1131-54 (2004).
Davidson et al., "Recombinant adeno-associated virus type 2, 4, and 5 vectors: Transduction of variant cell types and regions in the mammalian central nervous system", PNAS vol. 97 (7), 3428-3432 (2000).
Glorioso et al., "Therapeutic gene transfer to the nervous system using viral vectors", *J. Neurovirology* vol. 9, 165-172 (2003).
Govindasamy et al., "Structurally Mapping the Diverse Phenotype of Adeno-Associated Virus Serotype 4", *J. Vir*. 80(23), 11556-11570 (2006).
Liu et al., "Functional Correction of CNS Phenotypes in a Lysosomal Storage Disease Model Using Adeno-Associated Virus Type 4 Vectors," *J. Neurosecience*, 25(41), 9321-9327 (2005).

(Continued)

*Primary Examiner* — Brian Whiteman
(74) *Attorney, Agent, or Firm* — Viksnins Harris Padys Malen LLP

(57) ABSTRACT

The present disclosure provides methods of treating a disease in a non-rodent mammal comprising administering to the cerebrospinal fluid (CSF) of the non-rodent mammal an rAAV2 particle containing a vector comprising a nucleic acid encoding a therapeutic protein inserted between a pair of AAV inverted terminal repeats in a manner effective to infect an ependymal cell in the non-rodent mammal, wherein the ependymal cell secretes the therapeutic protein so as to treat the disease.

24 Claims, 15 Drawing Sheets

(56) References Cited

OTHER PUBLICATIONS

Patent Cooperation Treaty, International Searching Authority, Search Report and Written Opinion for PCT/US2012/031896, 11 pages, dated Aug. 16, 2012.
Sondhi D et al., "AAV2-mediated CLN2 gene transfer to rodent and nonhuman primate brain results in long-term TPP-I expression compatible with therapy for LINCL", Gene Ther. 12(22), 1618-32 (2005).
Sondhi D et al., "Enhanced survival of the LINCL mouse following CLN2 gene transfer using the rh.10 rhesus macaque-derived adeno-associated virus vector", Mol. Ther. 15(3), 481-91 (2007).
Yamazaki et al., "Targeted gene transfer into ependymal cells through intraventricular injection of AAV1 vector and long-term enzyme replacement via the CSF", Scientific Reports 4, 5506, 7 pages (2014).
Cook, et al., "Intracerebroventricular Administration of Drugs", Pharmacotherapy, 29 (7), 832-845, (2009).
Del Bigio, et al., "Fine Structure of Astroglial Integration into Host Brain Following Xenografting", Journal of Neuropathology and Experimental Neurology vol. 54(3), 385-394 (1995).
Del Bigio, "Letter to the Editor", Journal of Neuropathology and Experimental Neurology vol. 54 (3), 405 (1995).
Del Bigio, et al., "The Ependyma: A Protective Barrier Between Brain and Cerebrospinal Fluid", GLIA 14, 1-13 (1995).
Ghodsi, et al., "Systemic Hyperosmolality Improves β-Glucuronidase Distribution and Pathology in Murine MPS VII Brain Following Intraventricular Gene Transfer", Experimental Neurology 160, 109-116 (1999).
Hachiya, et al., "Mechanisms of neurodegeneration in neuronal ceroid-lipofuscinoses", Acta Neuropathol 111, 168-177 (2006).
Katz, et al., "Enzyme Replacement Therapy Attenuates Disease Progressionin a Canine Model of Late-Infantile Neuronal Ceroid Lipofuscinosis (CLN2 Disease)", Journal of Neuroscience Research 92, 1591-1598 (2014).
Liu, et al., "Structural Organization and Sequence of CLN2, the Defective Gene in Classical Late Infantile Neuronal Ceroid Lipofuscinosis", Genomics 50, 206-212 (1998).
Mole, et al., "Genetics of the neuronal ceroid lipofuscinoses (Batten disease)", Biochimica et Biophysica Acta 1852, 2237-2241 (2015).

Orlin, et al., "Spectrum of Ocular Manifestations in CLN2-Associated Batten (Jansky-Bielschowsky) Disease Correlate with Advancing Age and Deteriorating Neurological Function", PLoS One, vol. 8(8), e73128, 13 pages (2013).
Passini, et al., "Intracranial Delivery of CLN2 Reduces Brain Pathology in a Mouse Model of Classical Late Infantile Neuronal Ceroid Lipofuscinosis", Journal of Neuroscience 26(5), 1334-1342 (2006).
Passini, et al., "Intraventricular Brain Injection of Adeno-Associated Virus Type 1 (Aav1) in Neonatal Mice Results in Complementary Patters of Neuronal Transduction to Aav2 and Total Long-Term Correction of Storage Lesions in the Brains of Glucuronidase-Deficient Mice", Journal of Virology, vol. 77, No. 12, 7034-7040 (2003).
Perez-Poyato, et al., "Late Infantile Neuronal Ceroid Lipofuscinosis: Mutations in the CLN2 Gene and Clinical Course in Spanish Patients", Journal of Child Neurology 28(4), 470-478 (2012).
Sondhi, et al., "Feasibility of Gene Therapy for Late Neuronal Ceroid Lipofuscinosis", Arch Neurol 58, 1793-1798 (2001).
Sondhi, et al., "Long-Term Expression and Safety of Administration of AAVrh.10hCLN2 to the Brain of Rats and Nonhuman Primates for the Treatment of Late Infantile Neuronal Ceroid Lipofuscinosis", Human Gene Therapy Methods 23, 324-335 (2012).
Souweidane, et al., "Gene therapy for late infantile meuronal ceroid lipofuscinosis: neurosurgical considerations", J Neurosurg Pediatrics 6, 115-122 (2010).
Vuillemenot, et al., "Nonclinical evaluation of CNS-administered TPP1 enzyme replacement in canine CLN2 neuronal ceroid lipofuscinosis", Molecular Genetics and Metabolism 114, 281-293 (2015).
Vuillemenot, et al., "Recombinant human tripeptidyl peptidase-1 infusion to the monkey CNS: Safety, pharmacokinetics, and distribution", Toxicology and Applied Pharmacology 277, 49-57 (2014).
Walus, et al., "Functional Consequences and Rescue Potential of Pathogenic Missense Mutations in Tripeptidyl Peptidase I", Hum Mutat 31, 710-721 (2010).
Xu, et al., "Large-Volume Intrathecal Enzyme Delivery Increases Survival of a Mouse Model of Late Infantile Neuronal Ceroid Lipofuscinosis", American Society of Gene & Cell Therapy, www.moleculartherapy.org vol. 19(10), 1842-1848 (2011).

* cited by examiner

AAVeGFP in nonhuman primate brain

Figure 6A-1

ClustalW (v1.83) multiple sequence alignment

2 Sequences Aligned          Alignment Score = nan
Gaps Inserted = 7            Conserved Identities = 446

Pairwise Alignment Mode: Slow
Pairwise Alignment Parameters:
 Open Gap Penalty = 10.0     Extend Gap Penalty = 0.1
 Similarity Matrix: gonnet Multiple Alignment Parameters:
 Open Gap Penalty = 10.0     Extend Gap Penalty = 0.1
 Delay Divergent = 40%       Gap Distance = 8
 Similarity Matrix: gonnet Processing time: 0.2 seconds

```
AAV4capPro    1 -MTDGYLPDWLEDNLSEGVREWWALQPGAPKPKANQQHQDNARGLVLPGYKYLGPNGLD   59
AAV2capPro    1 MAADGYLPDWLEDTLSEGIRQWWKLKPGPPPKPAERHKDDSRGLVLPGYKYLGPFNGLD   60
                 *************.*****.******:*::**** ***  *.*.* .************ ****

AAV4capPro   60 KGEPVNAADAAALEHDKAYDQQLKAGDNPYLKYNHADAEFQQRLQGDTSFGGNLGRAVFQ  119
AAV2capPro   61 KGEPVNEADAAALEHDKAYDRQLDSGDNPYLKYNHADAEFQERLKEDTSFGGNLGRAVFQ  120
                ****** ************:**..******************:**..****************

AAV4capPro  120 AKKRVLEPLGLVEQAGETAPGKKRPLIESPQQPDSSTGIGKKGKQPAKKKLVFEDETGAG  179
AAV2capPro  121 AKKRVLEPLGLVEEPVKTAPGKKRPVEHSPVEPDSSSGTGKAGQQPARKRLNFGQTGDAD  180
                *************   .*******:*.** :*** *.**..****:*:*.*.:**.*
```

Figure 6A-2

```
AAV4capPro  180 DGP---PEGSTSGAMS--DDSEMRAAAGGAAVEGGQGADGVGNASGDWHCDSTWSEGHVT 234
AAV2capPro  181 SVPDPQPLGQPPAAPSGLGTNTMATGSGAPMADNNEGADGVGNSSGNWHCDSTWMGDRVI 240
                 *      *       *      *  * *  *   *      *********** *   *

AAV4capPro  235 TTSTRTWVLPTYNNHLYKRLG---ESLQSNTYNGFSTPWGYFDFNRFHCHFSPRDWQRLI 291
AAV2capPro  241 TTSTRTWALPTYNNHLYKQISSQSGASNDNHYFGYSTPWGYFDFNRFHCHFSPRDWQRLI 300
                ******* **********       *  *   *  *********************

AAV4capPro  292 NNNWGMRPKAMRVKIFNIQVKEVTTSNGETTVANNLTSTVQIFADSSYELPYVMDAGQEG 351
AAV2capPro  301 NNNWGFRPKRLNFKLFNIQVKEVTQNDGTTTIANNLTSTVQVFTDSEYQLPYVLGSAHQG 360
                *****  ** *   *********   * ** ********.* ** **  *** *   *

AAV4capPro  352 SLPPFPNDVFMVPQYGYCGLVTGNTSQQQTDRNAFYCLEYFPSQMLRTGNNFEITYSFEK 411
AAV2capPro  361 CLPPFPADVFMVPQYGYLTLNNG---SQAVGRSSFYCLEYFPSQMLRTGNNFTFSYTFED 417
                 ***** *********     *      *     ****************  :*  *

AAV4capPro  412 VPFHSMYAHSQSLDRLMNPLIDQYLWGLQSTTTGTTLNAGTATTNFTKLRPTNFSNFKKN 471
AAV2capPro  418 VPFHSSYAHSQSLDRLMNPLIDQYLYLSRTNTPSGTTT-QSRLQFSQAGASDIRDQSRN 476
                ***** ******************   *   * ***      *   .        *

AAV4capPro  472 WLPGPSIKQQGFSKTANQNYKIPATGSDLIKYETHSTLDGRWSALTPGPPMATAGPADS 531
AAV2capPro  477 WLPGPCYRQQRVSKTSADNNNSEYSWTG----ATKYHLNGRDSLVNPGPAMASHKDDEE 531
                *****  **  **** *    *   *        **      ***  **  .

AAV4capPro  532 KFS-NSQLIFAGPKQNGNTATVPGTLIFTSEEELAATNATDTDMWGNLPGGDQSNSNLPT 590
AAV2capPro  532 KFFPQSGVLIFGKQGSEKTNVDIEKVMITDEEEIRTTNPVATEQYGSVSTNLQRGNRQAA 591
                **    * *** ** *   *     * * ***  **  *   *  * **** * *  .
```

Figure 6A-3

```
AAV4capPro  591 VDRLTALGAVPGMVWQNRDIYYQGPIWAKIPHTDGHFHPSPLIGGFGLKHPPPQIFIKNT 650
AAV2capPro  592 TADVNTQGVLPGMVWQDRDVYLQGPIWAKIPHTDGHFHPSPLMGGFGLKHPPPQILIKNT 651
                 :.*   ..***  **:* ** .****************** :***********:****

AAV4capPro  651 PVPANPATTFSSTPVNSFITQYSTGQVSVQIDWEIQKERSKRWNPEVQFTSNYGQQNSLL 710
AAV2capPro  652 PVPANPSTTFSAAKFASFITQYSTGQVSVEIEWELQKENSKRWNPEIQYTSNYNKSVNVD 711
                ******:***:: .:************:::**:***.******:*:****  . :

AAV4capPro  711 WAPDAAGKYTEPRAIGTRYLTHHL 734
AAV2capPro  712 FTVDTNGVYSEPRPIGTRYLTRNL 735
                :: .: .  :***.******..*
```

Figure 6B-1

ClustalW (v1.83) multiple sequence alignment

2 Sequences Aligned          Alignment Score = nan
Gaps Inserted = 10           Conserved Identities = 1440

Pairwise Alignment Mode: Slow
Pairwise Alignment Parameters:
    Open Gap Penalty = 10.0      Extend Gap Penalty = 5.0

Multiple Alignment Parameters:
    Open Gap Penalty = 30.0      Extend Gap Penalty = 5.0
    Delay Divergent = 40%        Transitions: Weighted Processing time: 1.8 seconds 1. AAV2capNuc vs. AAV4capNucl Aligned Length = 2235    Gaps = 10
    Identities = 1440 (65%)

```
AAV2capNuc    1 ATGGCTGCCGATGGTTATCTTCCAGATTGGCTCGAGGACACTCTCTCTGAAGGAATAAGA    60
AAV4capNucl   1 ---ATGACTGACGGTTACCTTCCAGATTGGCTAGAGAGACAACCTCTCTGAAGGCGTTCGA    57
                   ** ****  ***************** *  ***  *********** **********   *  **

AAV2capNuc   61 CAGTGGTGGAAGCTCAAACCTGGCCACCACCACCAAAGCCCGCAGAGCGGCATAAGGAC   120
AAV4capNucl  58 GAGTGGTGGGCGCTGCAACCTGGAGCCCCTAAACCCAAGGCAAATCAACAACATCAGGAC   117
                 ********* *** ****** * *** *** * * *** ***** **  * *** ******
```

Figure 6B-2

```
AAV2capNuc  121 GACAGCAGGGGTCTTTGTGCTTCCTGGGTACAAGTACCTCGGACCCTTCAACGGACTCGAC 180
AAV4capNuc1 118 AACGCTCGGGGTCTTTGTGCTTCCGGGTTACAAATACCTCGGACCGGACGGACTCGAC   177
                ** ****** ************** ** ****** *** ***** **** **** ******

AAV2capNuc  181 AAGGGAGAGCCGGTCAACGAGGCAGACGCCCGGCCCTCGAGCACGACAAAGCCTACGAC   240
AAV4capNuc1 178 AAGGGGGAACCCGTCAACGACGCCAGCGCCGACGCCCTCGAGCACGACAAGGCCTACGAC 237
                ***** ** ** ******** ** ** *** * ********* ***** ********

AAV2capNuc  241 CGGCAGCTCGACAGCGGAGACAACCCGTACCTCAAGTACAACCACGCCGACGCGGAGTTT 300
AAV4capNuc1 238 CAGCAGCTCAAGGCCGGTGACAACCCCTACCTCAAGTACAACCACGCCGACGCGGAGTTC 297
                * ******* *  *** ******** *****************************

AAV2capNuc  301 CAGGAGCGCCTTAAAGAAGATACGTCTTTTGGGGCAACCTCGGACGAGCAGTCTTCCAG  360
AAV4capNuc1 298 CAGCAGCGGCTTCAGGGCGACACATCGTTTGGGGCAACCTCGGACAGAGCAGTCTTCCAG 357
                *** **** *** *  *  ** ** * *************** * *************

AAV2capNuc  361 GCGAAAAAGAGGGTTCTTGAACCTCTGGGCCTGGTTGAGGAACCTGTTGAAGACGGCTCCG 420
AAV4capNuc1 358 GCCAAAAAGAGAGGGTTCTTGAACCTCTTGGTCTTGGTTGAGCAAGCGGGTGAGACGGCTCCT 417
                ** ********   *************  ** ** ******* **  * * ***********

AAV2capNuc  421 GGAAAAAAGAGAGGCCGGTAGAGCACTCTCCTGTGAGCCAGACTCCTCCTCGGGAACCGGA 480
AAV4capNuc1 418 GGAAAGAAGAGACCGTTGATTGAATCCCCCCAGCAGCCCGACTCCTCCTCCACGGTATCGGC 477
                ***** ****** ** *   ** *  **** **  ****************  **  * **

AAV2capNuc  481 AAGGCGGGCCAGCAGCCTGCAAGAAAAAAGATTGAATTTTGGTCAGACTGGAGACGCAGAC 540
AAV4capNuc1 478 AAAAAGGCAAGCAGCCGGCTAAAAAGAAGAAGCTCGTTTTCGA------AGACGAAACT 528
                **  ***** ******  **  ** *** *  ***  *** ***       ***** ***
```

Figure 6B-3

```
AAV2capNuc   541 TCAGTACCTGACCCCCAGCCTCTCGGACAGCCACCAGCAGCCCCTCTGGTCTGGGAACT 600
AAV4capNucl  529 GGAGCAGGCGACGGACCCCCTGAGGGATCAACTTCCGGAGCCATGTCTGAT-----GAC 582
                     *    ***   *  ****  * *   ***   * **** *****    ****  *

AAV2capNuc   601 AATACGATGGCTACAGGCAGTGGCGCCACCAATGGCAGACAATAACGAGGGCGCCGACGGA 660
AAV4capNucl  583 AGTGAGATGCGTGCAGCAGCTGGCGGAGCTGCAGTGCAGTCGAGGGGACAAGGTGCCGATGGA 642
                  * * ****  * *      * ***** *  **  **   * **  * ** * **** ***

AAV2capNuc   661 GTGGGTAATTCCTCGGGAAATTGGCATTGCGATTCCACATGGATGGGCGACAGAGTCATC 720
AAV4capNucl  643 GTGGGTAATGCCTCGGGTGATTGGCATTGGCATTCCACCTGGTCTGAGGGCCACGTCACG 702
                 ********* ******* ********** * ****** ***  *  *  **  ****

AAV2capNuc   721 ACCACCAGCACCCGAACCTGGGCCCTGCCCACTACAACAACCACCTCTACAAACAAATT 780
AAV4capNucl  703 ACCACCAGCAGAACCTGGCTTGCCACTGGGTCTTGCCCACTACAACAACCACCTCTACAAGCGACTC 762
                 ********** *     **  *  * **  * ** *********************** * *

AAV2capNuc   781 TCCAGCCAATCAGGAGCCTCGAACGACAATCACTACTTTGGCTACAGCACCCCTTGGGGG 840
AAV4capNucl  763 GG------AGAGAGCCTGCAGTCGCAACCTGCAACACCTACAACGGATTCTCCACCCCCTGGGGA 813
                  *       * * ****   *  **  ** ** **  ****  ** **  ******* *****

AAV2capNuc   841 TATTTTGACTTCAACAGATTCCACTGCCACTTTTCACCACGTGACTGGCAAAGACTCATC 900
AAV4capNucl  814 TACTTTGACTTCAACCGCTTCCACTGCCACTTCTCCCCACGTGACTGGCAGCGACTCATC 873
                 ** ************ * ************* **  ************* **********

AAV2capNuc   901 AACAACAACTGGGGATTCCGACCCAAGAGACTTCAACTTCAAGCTCTTTAACATTCAAGTC 960
AAV4capNucl  874 AACAACAACTGGGGCATGCCGACCCAAAGCCATGCCGGGGTCAAAATCTTCAACATCTTCAGTC 933
                 **************    ***** ****  *  **  *****   ****** **
```

Figure 6B-4

```
AAV2capNuc   961 AAAGAGGTCACGCAGAATGACGGTACGACGACGATTGCCAATAACCTTACCAGCACGTT 1020
AAV4capNucl  934 AAGGAGGTCACGACGTCGAACGGCGAGACAACGGTGGCTAATAACCTTACCAGCACGTT 993
                 *** ********** *   ***    ** *** *** **  ** *************

AAV2capNuc  1021 CAGGTGTTTACTGACTCGGAGTACCAGTCCCCGTACGTCCTCGGCTCGGCGCATCAAGGA 1080
AAV4capNucl  994 CAGATCTTTGCGGACTCGTCGTACGAACTGCCGTACGTGATGGATGCGGGTCAAGAGGGC 1053
                 ***  * ** * ***** * ***  *   **** **** ** **  * * *** * *

AAV2capNuc  1081 TGCCTCCGCCGCGTTCCCAGCAGAGCTCTTCATGGTGCCACAGTATGGATACCTCACCCTG 1140
AAV4capNucl 1054 AGCCTGCCTCCTTTTCCCAACGACTGCTCTTTATGGTGCCCCAGTACGGCTACTGTGGACTG 1113
                  ***** **  * ** *** * **  ****** ******* ***** ** ***   ***

AAV2capNuc  1141 AACAACGGGAGT--CAGGCAGTAGGACGCTC------TTCATTTTACTGCCTGGAGTAC 1191
AAV4capNucl 1114 GTGACCGGCAACACTTCGCAGCAACAGACTGACAGAAATGCCTTCTACTGCCTGGAGTAC 1173
                   ***  *      *** ***  *  **  *       *  *    * ************

AAV2capNuc  1192 TTTCCTTCTCAGATGCTGCGGACGGAAACAACTTTACCTTCAGCTACACACTTTTGAGGAC 1251
AAV4capNucl 1174 TTTCCTTCGCAGATGCTGCGGACTGGGAACAACTTTGAAATTACGTACAGTTTTGAGAAG 1233
                 ******** ************** *  ********* **  *** ****  ******  *

AAV2capNuc  1252 GTTCCTTTCCACAGCAGCAGTACGGCTCACAGAGCCAGAGTCTGGACCGTCTCATGAATCCTCTC 1311
AAV4capNucl 1234 GTGCCTTTCCACTCGATGTACGCGCAGAGCCAGAGCCTGGACCGGCTGATGAACCCTCTC 1293
                 ** ********    *  * ****  **  ***** ** **** ** *** ** ******

AAV2capNuc  1312 ATCGACCAGTACCTGTATTACTTGAGCAGAACAAACACTCCAAGTGGAACCACCACGCAG 1371
AAV4capNucl 1294 ATCGACCAGTACCTGTGGGGACTGCAATGCGAATGCGACCACCCCTGAATGCCGGG 1353
                 **************** *  * *  *   **  *    *** * * ** *   * 
```

Figure 6B-5

```
AAV2capNuc  1372 TCAA--GGCTTCAGTTTTCTCAGGCCGGAGCG-AGTGACATTCGGGACCAGTCTAGGAAC 1428
AAV4capNucl 1354 ACTGCCACCACCAACTTTACCAAGCTGCGGCCTACCAACTTTTCCAACTTTAAAAGAAC 1413
                      *  **  ***   **   ** *  ****   ** * *** *   ****

AAV2capNuc  1429 TGGCTTCCTGGACCCTGTTACCGCCAGCAGCGAGTATCAAAGACATCTGCGGATAACAAC 1488
AAV4capNucl 1414 TGGCTGCCCGGGCCTTCAATCAAGCAGCAGCAGGGCTTCTCAAAGACTGCCAATCAAACTAC 1473
                 ***** **  *** ** * **  ***  **  **     ** ***** **  **  * **

AAV2capNuc  1489 AACAG---TGAATACTCGTGGACTGGAGCTACCAAGTACCA--------CCTCAAT 1533
AAV4capNucl 1474 AAGATCCCTGCCACCGGGTCAGACAGTCTCATCAAATACGAGACGCACAGCACTCTGGAC 1533
                 **  *    *  *  * *     *  *  *** *** **           **  *

AAV2capNuc  1534 GGCAGAGACTCTCTGGTGAATCCGGCCCGGCCCATGCAAGCCACAAGGACGATGAAGAA 1593
AAV4capNucl 1534 GGAAGATGGAGTGCCCTGACCCCCGACCTCCAATGGCCACGGCTGGACCTGCGGACAGC 1593
                 **  **    * *  **   *  *** *   **** * **    ***       *  *

AAV2capNuc  1594 AAGTTTTTCCTCAGAGCGGGTTCTCATCTTTGGGAAGCAAGGCTCAGAGAAAACAAAT 1653
AAV4capNucl 1594 AAGTTCAG---CAACAGCCAGCTCATCTTCACCTCTAAACAGAACGGCAACACGGCC 1650
                 *****        *  **   * ****** *  ***     ***  **  **  ***

AAV2capNuc  1654 GTGGACATTGAAAAGGTCATGATTACAGACGAAGAGAGGAAATCAGGACACCAATCCCGTG 1713
AAV4capNucl 1651 ACCGTACCCGGGACTCTGATCTTCACCTCTGAGGAGGAGCTGGCAGCCAACGCCACC 1710
                   *    *  ** *   ****  *      *** *   **        ** *  ***

AAV2capNuc  1714 GCTACGGAGCAGTATGGTTCTGTATCTACCAACCTCCAGAGAGGCAACAGACAAGCAGCT 1773
AAV4capNucl 1711 GATACGGACACATGTGGGCAACCTACCTGGCGGTGACCAGAGCAACAGCAACCTGCCGACC 1770
                   ******    **** *     * **   *   *  ***   ***   ** * ***
```

Figure 6B-6

```
AAV2capNuc  1774 ACCGCAGATGTCAACACACAAGGCGTTCTTCCAGGCATGGTCTGGCAGGACAGAGATGTG 1833
AAV4capNucl 1771 GTGGACAGACTGACAGCCTTGGGAGCCGTGCCTGAATGGTCTGGCAAAACAGAGACATT 1830
                   *  ** *****  ***  ***   ***  ** ****** *********  ********  *

AAV2capNuc  1834 TACCTTCAGGGGCCCATCTGGGCAAAGATTCCACACACGGACGGACATTTTCACCCTCT 1893
AAV4capNucl 1831 TACTACCAGGGTCCCATTTGGGCCAAGATTCCTCATACCGATGGACACTTTCACCCTCA 1890
                 *** ** ***** ***** ***** ******** **  *  ** ****** ******** *

AAV2capNuc  1894 CCCCTCATGGGTGGATTCGGACTTAAACACCCCTCCTCCACAGATTCTCATCAAGAACACC 1953
AAV4capNucl 1891 CCGCTGATTGGTGGGTTTGGGCTGAAACACCCGCCTCCTCAAATTTTATCAAGAACACC 1950
                 ** ** ** ****** **  *  *******  **  ** ** *** * *************

AAV2capNuc  1954 CCGGTACCTGCGAATCCTTCGACCACCTTCAGTGCGGCAAAGTTTGCTTCCTTCATCACA 2013
AAV4capNucl 1951 CCGGTACCTGCGAATCCTGCAACGACCTTCAGCTCCGGTAACTCCGGTAAACTCCTTCATTACT 2010
                 ******************  * **  ***  *** ****** ********  * ** ********  **

AAV2capNuc  2014 CAGTACTCCACGGACAGGTCAGCGTGGAGATCGAGTGGGAGCTGCAGAAGGAAAACAGC 2073
AAV4capNucl 2011 CAGTACAGCACTGGCCAGTGTGGTCGAGATTGACTGGGAGATCCAGAAGGAGGAGCGGTCC 2070
                 ******  *** ** ***** *** ***** ** ******  * ** *****  * *******  *

AAV2capNuc  2074 AAACGCTGGAATCCCGAAATTCAGTACACTTCCAACTACAACAAGTCTGTTAATGTGGAC 2133
AAV4capNucl 2071 AAACGCTGGAACCCCGAGTCCAGTTCCAGTTTACCTCCAACTACGACGACAGCAAAACTCTCGTTG 2130
                 *********** ***** * **** ** **** * * ** ******** **  *****  **

AAV2capNuc  2134 TTTACTGTGGACACTAATGGCGTGTATTCAGAGCCTCGCCCCATTGGCACCAGATACCTG 2193
AAV4capNucl 2131 TGGGCTCCCGATGCGGGCTGGGAAATACACTGAGCCTATCGGTACCTACCCGCTACCTC 2190
                   *       ***  * **  ** * *********  * * ****  * ****** ***
```

Figure 6B-7

```
AAV2capNuc   2194 ACTCGTAATCTGTAA 2208
AAV4capNucl  2191 ACCCACCACCTGTAA 2205
                  ** * *  * ******
```

METHODS AND COMPOSITIONS FOR TREATING BRAIN DISEASES

PRIORITY OF INVENTION

This application claims priority to U.S. Provisional Application No. 61/470,460 that was filed on Mar. 31, 2011. The entire content of this provisional application is hereby incorporated herein by reference.

FEDERAL GRANT SUPPORT

This invention was made with government support under NS068099 awarded by National Institutes of Health. The government has certain rights in the invention.

BACKGROUND

Gene transfer is now widely recognized as a powerful tool for analysis of biological events and disease processes at both the cellular and molecular level. More recently, the application of gene therapy for the treatment of human diseases, either inherited (e.g., ADA deficiency) or acquired (e.g., cancer or infectious disease), has received considerable attention. With the advent of improved gene transfer techniques and the identification of an ever expanding library of defective gene-related diseases, gene therapy has rapidly evolved from a treatment theory to a practical reality.

Traditionally, gene therapy has been defined as a procedure in which an exogenous gene is introduced into the cells of a patient in order to correct an inborn genetic error. Although more than 4500 human diseases are currently classified as genetic, specific mutations in the human genome have been identified for relatively few of these diseases. Until recently, these rare genetic diseases represented the exclusive targets of gene therapy efforts. Accordingly, most of the NIH approved gene therapy protocols to date have been directed toward the introduction of a functional copy of a defective gene into the somatic cells of an individual having a known inborn genetic error. Only recently, have researchers and clinicians begun to appreciate that most human cancers, certain forms of cardiovascular disease, and many degenerative diseases also have important genetic components, and for the purposes of designing novel gene therapies, should be considered "genetic disorders." Therefore, gene therapy has more recently been broadly defined as the correction of a disease phenotype through the introduction of new genetic information into the affected organism.

In in vivo gene therapy, a transferred gene is introduced into cells of the recipient organism in situ that is, within the recipient. In vivo gene therapy has been examined in several animal models. Several recent publications have reported the feasibility of direct gene transfer in situ into organs and tissues such as muscle, hematopoietic stem cells, the arterial wall, the nervous system, and lung. Direct injection of DNA into skeletal muscle, heart muscle and injection of DNA-lipid complexes into the vasculature also has been reported to yield a detectable expression level of the inserted gene product(s) in vivo.

Treatment of diseases of the central nervous system, e.g., inherited genetic diseases of the brain, remains an intractable problem. Examples of such are the lysosomal storage diseases. Collectively, the incidence of lysosomal storage diseases (LSD) is 1 in 10,000 births world wide, and in 65% of cases, there is significant central nervous system (CNS) involvement. Proteins deficient in these disorders, when delivered intravenously, do not cross the blood-brain barrier, or, when delivered directly to the brain, are not widely distributed. Thus, therapies for the CNS deficits need to be developed.

SUMMARY

The present invention provides a method of delivering a nucleic acid to an ependymal cell of a non-rodent mammal comprising administering to the ependymal cell an AAV2 particle containing a vector comprising the nucleic acid inserted between a pair of AAV2 inverted terminal repeats, thereby delivering the nucleic acid to the ependymal cell. In certain embodiments, the rAAV2 particle infects the non-primate ependymal cell at an rate of more than 20% than the infectivity rate of AAV4, such as at a rate of more than 50% or 100%, 1000% or 2000% than the infectivity rate of AAV4.

The present invention provides a method of delivering a nucleic acid to a non-rodent mammal comprising administering to an ependymal cell from the mammal an AAV2 particle comprising the nucleic acid inserted between a pair of AAV inverted terminal repeats, and returning the ependymal cell to the mammal, thereby delivering the nucleic acid to the mammal.

The present invention provides a method of delivering a nucleic acid to an ependymal cell in a non-rodent mammal comprising administering to the mammal an AAV2 particle comprising the nucleic acid inserted between a pair of AAV inverted terminal repeats, thereby delivering the nucleic acid to an ependymal cell in the mammal.

The present invention provides a method to deliver an agent to the central nervous system of a non-rodent mammal, comprising administering to the cerebrospinal fluid (CSF) of the non-rodent mammal an AAV2 particle containing a vector comprising the nucleic acid inserted between a pair of AAV inverted terminal repeats in a manner effective to infect ependymal cells in the non-rodent mammal such that the ependymal cells secret the agent into the CSF of the non-rodent mammal.

The present invention provides a method of treating a disease in a non-rodent mammal comprising administering to the ependymal cells of the mammal an AAV2 particle containing a vector comprising the nucleic acid inserted between a pair of AAV inverted terminal repeats, thereby delivering the nucleic acid to the ependymal cell.

In certain embodiments, the disease is a lysosomal storage disease (LSD). In certain embodiments, the LSD is infantile or late infantile ceroid lipofuscinoses, neuronopathic Gaucher, Juvenile Batten, Fabry, MLD, Sanfilippo A, Hunter, Krabbe, Morquio, Pompe, Niemann-Pick C, Tay-Sachs, Hurler (MPS-I H), Sanfilippo B, Maroteaux-Lamy, Niemann-Pick A, Cystinosis, Hurler-Scheie (MPS-I H/S), Sly Syndrome (MPS VII), Scheie (MPS-I S), Infantile Batten, GM1 Gangliosidosis, Mucolipidosis type II/III, or Sandhoff disease. In certain embodiments, the disease is LINCL. In certain embodiments, the disease is a neurodegenerative disease, such as Huntington's disease, ALS, hereditary spastic hemiplegia, primary lateral sclerosis, spinal muscular atrophy, Kennedy's disease, Alzheimer's disease, a polyglutamine repeat disease, or Parkinson's disease.

In certain embodiments, the large mammal is a primate, horse, sheep, goat, pig, or dog. In certain embodiments, the primate is a human.

In certain embodiments, the nucleic acid is a lysosomal hydrolase. In certain embodiments, the nucleic acid is TPP1.

The present invention provides a method of transfecting an ependymal cell a non-rodent mammalian brain comprising administering to the cerebrospinal fluid (CSF) of the non-rodent mammal an AAV2 particle containing a vector comprising a nucleic acid inserted between a pair of AAV2 inverted terminal repeats in a manner effective to infect ependymal cells in the non-rodent mammal such that the ependymal cells secrete the agent into the CSF of the non-rodent mammal.

The present invention provides a use of the viral vector described hereinabove to prepare a medicament useful for treating a lysosomal storage disease in a mammal.

The present invention provides a cell as described hereinabove for use in medical treatment or diagnosis.

The present invention provides a use of the cell as described hereinabove to prepare a medicament useful for treating a lysosomal storage disease in a mammal.

BRIEF DESCRIPTION OF THE DRAWINGS

FIG. 6A is an alignment of AAV2 (SEQ ID NO:1) and AAV4 (SEQ ID NO:2) proteins and FIG. 6B is and alignment of AAV2 (SEQ ID NO:3) and AAV4 (SEQ ID NO:4) nucleotides based on the sequence from AAV2 (NC_001401) and AAV4 (NC_001829).

DETAILED DESCRIPTION

Figure 1:
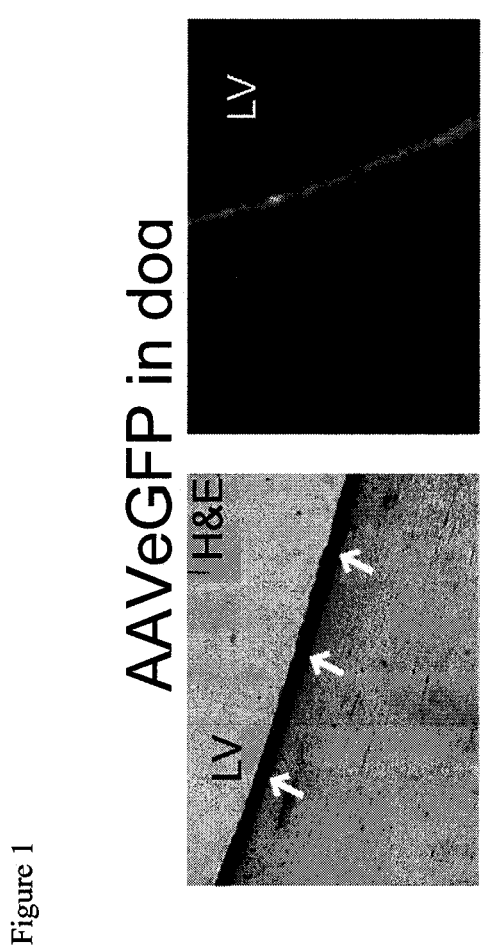
FIG. 1 shows the transfection of AAVeGFP in dog.

Adeno associated virus (AAV) is a small nonpathogenic virus of the parvoviridae family. AAV is distinct from the other members of this family by its dependence upon a helper virus for replication. In the absence of a helper virus, AAV may integrate in a locus specific manner into the q arm of chromosome 19. The approximately 5 kb genome of AAV consists of one segment of single stranded DNA of either plus or minus polarity. The ends of the genome are short inverted terminal repeats which can fold into hairpin structures and serve as the origin of viral DNA replication. Physically, the parvovirus virion is non-enveloped and its icosohedral capsid is approximately 20 nm in diameter.

To-date eight serologically distinct AAVs have been identified and five have been isolated from humans or primates and are referred to as AAV types 1-5. Govindasamy et al., "Structurally Mapping the Diverse Phenotype of Adeno-Associated Virus Serotype 4," *J. Vir.*, 80 (23):11556-11570 (2006). The genome of AAV2 is 4680 nucleotides in length and contains two open reading frames (ORFs). The left ORF encodes the non-structural Rep proteins, Rep 40, Rep 52, Rep 68 and Rep 78, which are involved in regulation of replication and transcription in addition to the production of single-stranded progeny genomes. Furthermore, two of the Rep proteins have been associated with the preferential integration of AAV genomes into a region of the q arm of human chromosome 19. Rep68/78 has also been shown to possess NTP binding activity as well as DNA and RNA helicase activities. The Rep proteins possess a nuclear localization signal as well as several potential phosphorylation sites. Mutation of one of these kinase sites resulted in a loss of replication activity.

The ends of the genome are short inverted terminal repeats (ITR) which have the potential to fold into T-shaped hairpin structures that serve as the origin of viral DNA replication. Within the ITR region two elements have been described which are central to the function of the ITR, a GAGC repeat motif and the terminal resolution site (trs). The repeat motif has been shown to bind Rep when the ITR is in either a linear or hairpin conformation. This binding serves to position Rep68/78 for cleavage at the trs which occurs in a site- and strand-specific manner. In addition to their role in replication, these two elements appear to be central to viral integration. Contained within the chromosome 19 integration locus is a Rep binding site with an adjacent trs. These elements have been shown to be functional and necessary for locus specific integration.

The AAV2 virion is a non-enveloped, icosohedral particle approximately 25 nm in diameter, consisting of three related proteins referred to as VP1, VP2 and VP3. The right ORF encodes the capsid proteins VP1, VP2, and VP3. These proteins are found in a ratio of 1:1:10 respectively and are all derived from the right-hand ORF. The capsid proteins differ from each other by the use of alternative splicing and an unusual start codon. Deletion analysis has shown that removal or alteration of VP1 which is translated from an alternatively spliced message results in a reduced yield of infections particles. Mutations within the VP3 coding region result in the failure to produce any single-stranded progeny DNA or infectious particles. An AAV2 particle is a viral particle comprising an AAV2 capsid protein. An AAV2 capsid polypeptide can encode the entire VP1, VP2 and VP3 polypeptide. The particle can be a particle comprising AAV2 and other AAV capsid proteins (i.e., a chimeric protein, such as AAV4 and AAV2). Variations in the amino acid sequence of the AAV2 capsid protein are contemplated herein, as long as the resulting viral particle comprises the AAV2 capsid remains antigenically or immunologically distinct from AAV4, as can be routinely determined by standard methods. Specifically, for example, ELISA and Western blots can be used to determine whether a viral particle is antigenically or immunologically distinct from AAV4. Furthermore, the AAV2 viral particle preferably retains tissue tropism distinct from AAV4.

An AAV2 particle is a viral particle comprising an AAV2 capsid protein. An AAV2 capsid polypeptide encoding the entire VP1, VP2, and VP3 polypeptide can overall have at least about 63% homology (or identity) to the polypeptide having the amino acid sequence encoded by nucleotides set forth in SEQ ID NO:1 (AAV2 capsid protein). The capsid protein can have about 70% homology, about 75% homology, 80% homology, 85% homology, 90% homology, 95% homology, 98% homology, 99% homology, or even 100% homology to the protein set forth in SEQ ID NO:1. The capsid protein can have about 70% identity, about 75% identity, 80% identity, 85% identity, 90% identity, 95% identity, 98% identity, 99% identity, or even 100% identity to the protein set forth in SEQ ID NO:1. The particle can be a particle comprising both AAV4 and AAV2 capsid protein, i.e., a chimeric protein. Variations in the amino acid sequence of the AAV2 capsid protein are contemplated herein, as long as the resulting viral particle comprising the AAV2 capsid remains antigenically or immunologically distinct from AAV4, as can be routinely determined by standard methods. Specifically, for example, ELISA and Western blots can be used to determine whether a viral particle is antigenically or immunologically distinct from AAV4. Furthermore, the AAV2 viral particle preferably retains tissue tropism distinction from AAV4, such as that exemplified in the examples herein, though an AAV2 chimeric particle comprising at least one AAV2 coat protein may have a different tissue tropism from that of an AAV2 particle consisting only of AAV2 coat proteins.

As indicated in FIGS. 6A and 6B, AAV2 capsid sequence and AAV4 capsid sequence are about 60% homologous. In certain embodiments, the AAV2 capsid comprises (or consists of) a sequence that is at least 65% homologous to the amino acid sequence set forth in SEQ ID NO:1.

In certain embodiments, the invention further provides an AAV2 particle containing, i.e., encapsidating, a vector comprising a pair of AAV2 inverted terminal repeats. The nucleotide sequence of AAV2 ITRs is known in the art. Furthermore, the particle can be a particle comprising both AAV4 and AAV2 capsid protein, i.e., a chimeric protein. Moreover, the particle can be a particle encapsidating a vector comprising a pair of AAV inverted terminal repeats from other AAVs (e.g., AAV1-AAV8). The vector encapsidated in the particle can further comprise an exogenous nucleic acid inserted between the inverted terminal repeats.

The following features of AAV have made it an attractive vector for gene transfer. AAV vectors have been shown in vitro to stably integrate into the cellular genome; possess a broad host range; transduce both dividing and non dividing cells in vitro and in vivo and maintain high levels of expression of the transduced genes. Viral particles are heat stable, resistant to solvents, detergents, changes in pH, temperature, and can be concentrated on CsCl gradients. Integration of AAV provirus is not associated with any long term negative effects on cell growth or differentiation. The ITRs have been shown to be the only cis elements required for replication, packaging and integration and may contain some promoter activities.

The present invention provides methods of administering AAV2 particles, recombinant AAV2 vectors, and recombinant AAV2 virions. An AAV2 particle is a viral particle comprising an AAV2 capsid protein. A recombinant AAV2 vector is a nucleic acid construct that comprises at least one unique nucleic acid of AAV2. A recombinant AAV2 virion is a particle containing a recombinant AAV2 vector. To be considered within the term "AAV2 ITRs" the nucleotide sequence must retain one or both features described herein that distinguish the AAV2 ITR from the AAV4 ITR: (1) three (rather than four as in AAV4) "GAGC" repeats and (2) in the AAV2 ITR Rep binding site the fourth nucleotide in the first two "GAGC" repeats is a C rather than a T.

The promoter can be any desired promoter, selected by known considerations, such as the level of expression of a nucleic acid functionally linked to the promoter and the cell type in which the vector is to be used. Promoters can be an exogenous or an endogenous promoter. Promoters can include, for example, known strong promoters such as SV40 or the inducible metallothionein promoter, or an AAV promoter, such as an AAV p5 promoter. Additional examples of promoters include promoters derived from actin genes, immunoglobulin genes, cytomegalovirus (CMV), adenovirus, bovine papilloma virus, adenoviral promoters, such as the adenoviral major late promoter, an inducible heat shock promoter, respiratory syncytial virus, Rous sarcomas virus (RSV), etc. Specifically, the promoter can be AAV2 p5 promoter or AAV4 p5 promoter. Furthermore, smaller fragments of p5 promoter that retain promoter activity can readily be determined by standard procedures including, for example, constructing a series of deletions in the p5 promoter, linking the deletion to a reporter gene, and determining whether the reporter gene is expressed, i.e., transcribed and/or translated.

The AAV2 vector can further comprise an exogenous (heterologous) nucleic acid functionally linked to the promoter. By "heterologous nucleic acid" is meant that any heterologous or exogenous nucleic acid can be inserted into the vector for transfer into a cell, tissue or organism. The nucleic acid can encode a polypeptide or protein or an antisense RNA, for example. By "functionally linked" is meant such that the promoter can promote expression of the heterologous nucleic acid, as is known in the art, such as appropriate orientation of the promoter relative to the heterologous nucleic acid. Furthermore, the heterologous nucleic acid preferably has all appropriate sequences for expression of the nucleic acid, as known in the art, to functionally encode, i.e., allow the nucleic acid to be expressed. The nucleic acid can include, for example, expression control sequences, such as an enhancer, and necessary information processing sites, such as ribosome binding sites, RNA splice sites, polyadenylation sites, and transcriptional terminator sequences.

The heterologous nucleic acid can encode beneficial proteins that replace missing or defective proteins required by the subject into which the vector in transferred or can encode a cytotoxic polypeptide that can be directed, e.g., to cancer cells or other cells whose death would be beneficial to the subject. The heterologous nucleic acid can also encode antisense RNAs that can bind to, and thereby inactivate, mRNAs made by the subject that encode harmful proteins. In one embodiment, antisense polynucleotides can be produced from a heterologous expression cassette in an AAV2 viral construct where the expression cassette contains a sequence that promotes cell-type specific expression.

Examples of heterologous nucleic acids which can be administered to a cell or subject as part of the present AAV2 vector can include, but are not limited to the nucleic acids encoding therapeutic agents, such as lysosomal hydrolases; tumor necrosis factors (TNF), such as TNF-alpha; interferons, such as interferon-alpha, interferon-beta, and interferon-gamma; interleukins, such as IL-1, IL-1beta, and ILs-2 through -14; GM-CSF; adenosine deaminase; secreted factors such as growth factors; ion channels; chemotherapeutics; lysosomal proteins; anti-apoptotic gene products; proteins promoting neural survival such as glutamate receptors and growth factors; cellular growth factors, such as lymphokines; soluble CD4; Factor VIII; Factor IX; T-cell receptors; LDL receptor; ApoE; ApoC; alpha-1 antitrypsin; ornithine transcarbamylase (OTC); cystic fibrosis transmembrane receptor (CFTR); insulin; Fc receptors for antigen binding domains of antibodies, such as immunoglobulins; and antisense sequences which inhibit viral replication, such as antisense sequences which inhibit replication of hepatitis B or hepatitis non-A, non-B virus. Furthermore, the nucleic acid can encode more than one gene product, limited only by the size of nucleic acid that can be packaged.

An AAV2 particle is a viral particle comprising an AAV2 capsid protein. Variations in the amino acid sequence of the AAV2 capsid protein are contemplated herein, as long as the resulting viral particle comprising the AAV2 capsid remains antigenically or immunologically distinct from AAV4, as can be routinely determined by standard methods. Specifically, for example, ELISA and Western blots can be used to determine whether a viral particle is antigenically or immunologically distinct from other AAV serotypes.

The term "polypeptide" as used herein refers to a polymer of amino acids and includes full-length proteins and fragments thereof. Thus, "protein," polypeptide," and "peptide" are often used interchangeably herein. Substitutions can be selected by known parameters to be neutral. As will be appreciated by those skilled in the art, the invention also includes those polypeptides having slight variations in amino acid sequences or other properties. Such variations may arise naturally as allelic variations (e.g. due to genetic polymorphism) or may be produced by human intervention (e.g., by mutagenesis of cloned DNA sequences), such as induced point, deletion, insertion and substitution mutants. Minor changes in amino acid sequence are generally preferred, such as conservative amino acid replacements, small internal deletions or insertions, and additions or deletions at the ends of the molecules. These modifications can result in changes in the amino acid sequence, provide silent mutations, modify a restriction site, or provide other specific mutations.

The present method provides a method of delivering a nucleic acid to a cell comprising administering to the cell an AAV2 particle containing a vector comprising the nucleic acid inserted between a pair of AAV inverted terminal repeats, thereby delivering the nucleic acid to the cell. Administration to the cell can be accomplished by any means, including simply contacting the particle, optionally contained in a desired liquid such as tissue culture medium, or a buffered saline solution, with the cells. The particle can be allowed to remain in contact with the cells for any desired length of time, and typically the particle is administered and allowed to remain indefinitely. For such in vitro methods, the virus can be administered to the cell by standard viral transduction methods, as known in the art and as exemplified herein. Titers of virus to administer can vary, particularly depending upon the cell type, but will be typical of that used for AAV transduction in general. Additionally the titers used to transduce the particular cells in the present examples can be utilized. The cells can include any desired cell in humans as well as other large (non-rodent) mammals, such as primates, horse, sheep, goat, pig, and dog.

More specifically, the present invention provides a method of delivering a nucleic acid to an ependymal cell, comprising administering to the ependymal cell an AAV2 particle containing a vector comprising the nucleic acid inserted between a pair of AAV inverted terminal repeats, thereby delivering the nucleic acid to the ependymal cell.

The present invention also includes a method of delivering a nucleic acid to a subject comprising administering to a cell from the subject an AAV2 particle comprising the nucleic acid inserted between a pair of AAV inverted terminal repeats, and returning the cell to the subject, thereby delivering the nucleic acid to the subject. The AAV ITRs can be AAV2 ITRs. For such an ex vivo administration, cells are isolated from a subject by standard means according to the cell type and placed in appropriate culture medium, again according to cell type. Viral particles are then contacted with the cells as described above, and the virus is allowed to transfect the cells. Cells can then be transplanted back into the subject's body, again by means standard for the cell type and tissue. If desired, prior to transplantation, the cells can be studied for degree of transfection by the virus, by known detection means and as described herein.

The present invention further provides a method of delivering a nucleic acid to a cell in a subject comprising administering to the subject an AAV2 particle comprising the nucleic acid inserted between a pair of AAV inverted terminal repeats, thereby delivering the nucleic acid to a cell in the subject. Administration can be an ex vivo administration directly to a cell removed from a subject, such as any of the cells listed above, followed by replacement of the cell back into the subject, or administration can be in vivo administration to a cell in the subject. For ex vivo administration, cells are isolated from a subject by standard means according to the cell type and placed in appropriate culture medium, again according to cell type. Viral particles are then contacted with the cells as described above, and the virus is allowed to transfect the cells. Cells can then be transplanted back into the subject's body, again by means standard for the cell type and tissue. If desired, prior to transplantation, the cells can be studied for degree of transfection by the virus, by known detection means and as described herein.

Also provided is a method of delivering a nucleic acid to an ependymal cell in a subject comprising administering to the subject an AAV2 particle comprising the nucleic acid inserted between a pair of AAV inverted terminal repeats, thereby delivering the nucleic acid to an ependymal cell in the subject.

In certain embodiments, the amino acid sequence that targets brain vascular endothelium targets brain vascular endothelium in a subject that has a disease, e.g., a lysosomal storage disease.

In certain embodiments, the amino acid sequence that targets brain vascular endothelium targets brain vascular endothelium in a subject that does not have a lysosomal storage disease.

In certain embodiments, the viral vector comprises a nucleic acid sequence encoding a therapeutic agent. In certain embodiments, the therapeutic agent is TPP1.

Certain embodiments of the present disclosure provide a cell comprising a viral vector as described herein.

In certain embodiments, the cell is a mammalian cell of a non-rodent mammal. In certain embodiments, the cell is a primate cell. In certain embodiments, the cell is a human cell. In certain embodiments, the cell is a non-human cell. In certain embodiments, the cell is in vitro. In certain embodiments, the cell is in vivo. In certain embodiments, the cell is an ependymal cell.

Certain embodiments of the present disclosure provide a method of treating a disease in a mammal comprising administering a viral vector or the cell as described herein to the mammal.

In certain embodiments, the mammal is human.

In certain embodiments, the disease is a lysosomal storage disease (LSD). In certain embodiments, the LSD is infantile or late infantile ceroid lipofuscinoses, Gaucher, Juvenile Batten, Fabry, MLD, Sanfilippo A, Late Infantile Batten, Hunter, Krabbe, Morquio, Pompe, Niemann-Pick C, Tay-Sachs, Hurler (MPS-I H), Sanfilippo B, Maroteaux-Lamy, Niemann-Pick A, Cystinosis, Hurler-Scheie (MPS-I H/S), Sly Syndrome (MPS VII), Scheie (MPS-I S), Infantile Batten, GM1 Gangliosidosis, Mucolipidosis type II/III, or Sandhoff disease.

In certain embodiments, the disease is a neurodegenerative disease. In certain embodiments, the neurodegenerative disease is Huntington's disease, ALS, hereditary spastic hemiplegia, primary lateral sclerosis, spinal muscular atrophy, Kennedy's disease, Alzheimer's disease, a polyglutamine repeat disease, or Parkinson's disease.

Certain embodiments of the present disclosure provide a method to deliver an agent to the central nervous system of a subject, comprising administering to the CSF with a viral vector described herein so that the transduced ependymal cells express the therapeutic agent and deliver the agent to the central nervous system of the subject. In certain embodiments, the viral vector transduces ependymal cells.

Certain embodiments of the present disclosure provide a viral vector or cell as described herein for use in medical treatments.

Certain embodiments of the present disclosure provide a use of a viral vector or cell as described herein to prepare a medicament useful for treating a disease, e.g., a lysosomal storage disease, in a mammal.

The vector may further comprise a lysosomal enzyme (e.g., a lysosomal hydrolase), a secreted protein, a nuclear protein, or a cytoplasmic protein. As used herein, the term "secreted protein" includes any secreted protein, whether naturally secreted or modified to contain a signal sequence so that it can be secreted.

Nucleic acid is "operably linked" when it is placed into a functional relationship with another nucleic acid sequence. Generally, "operably linked" means that the DNA sequences being linked are contiguous. However, enhancers do not have to be contiguous. Linking is accomplished by ligation at convenient restriction sites. If such sites do not exist, the synthetic oligonucleotide adaptors or linkers are used in accordance with conventional practice. Additionally, multiple copies of the nucleic acid encoding enzymes may be linked together in the expression vector. Such multiple nucleic acids may be separated by linkers.

The present disclosure also provides a mammalian cell containing a vector described herein. The cell may be human, and may be from brain. The cell type may be a stem or progenitor cell population.

The present disclosure provides a method of treating a disease such as a genetic disease or cancer in a mammal by administering a polynucleotide, polypeptide, expression vector, or cell described herein. The genetic disease or cancer may be a lysosomal storage disease (LSD) such as infantile or late infantile ceroid lipofuscinoses, Gaucher, Juvenile Batten, Fabry, MLD, Sanfilippo A, Late Infantile Batten, Hunter, Krabbe, Morquio, Pompe, Niemann-Pick C, Tay-Sachs, Hurler (MPS-I H), Sanfilippo B, Maroteaux-Lamy, Niemann-Pick A, Cystinosis, Hurler-Scheie (MPS-I H/S), Sly Syndrome (MPS VII), Scheie (MPS-I S), Infantile Batten, GM1 Gangliosidosis, Mucolipidosis type II/III or Sandhoff disease.

The genetic disease may be a neurodegenerative disease, such as Huntington's disease, ALS, hereditary spastic hemiplegia, primary lateral sclerosis, spinal muscular atrophy, Kennedy's disease, Alzheimer's disease, a polyglutamine repeat disease, or focal exposure such as Parkinson's disease.

Certain aspects of the disclosure relate to polynucleotides, polypeptides, vectors, and genetically engineered cells (modified in vivo), and the use of them. In particular, the disclosure relates to a method for gene or protein therapy that is capable of both systemic delivery of a therapeutically effective dose of the therapeutic agent.

According to one aspect, a cell expression system for expressing a therapeutic agent in a mammalian recipient is provided. The expression system (also referred to herein as a "genetically modified cell") comprises a cell and an expression vector for expressing the therapeutic agent. Expression vectors include, but are not limited to, viruses, plasmids, and other vehicles for delivering heterologous genetic material to cells. Accordingly, the term "expression vector" as used herein refers to a vehicle for delivering heterologous genetic material to a cell. In particular, the expression vector is a recombinant adenoviral, adeno-associated virus, or lentivirus or retrovirus vector.

The expression vector further includes a promoter for controlling transcription of the heterologous gene. The promoter may be an inducible promoter (described below). The expression system is suitable for administration to the mammalian recipient. The expression system may comprise a plurality of non-immortalized genetically modified cells, each cell containing at least one recombinant gene encoding at least one therapeutic agent.

The cell expression system can be formed in vivo. According to yet another aspect, a method for treating a mammalian recipient in vivo is provided. The method includes introducing an expression vector for expressing a heterologous gene product into a cell of the patient in situ, such as via intravenous administration. To form the expression system in vivo, an expression vector for expressing the therapeutic agent is introduced in vivo into the mammalian recipient i.v., where the vector migrates via the vasculature to the brain.

According to yet another aspect, a method for treating a mammalian recipient in vivo is provided. The method includes introducing the target protein into the patient in vivo.

The expression vector for expressing the heterologous gene may include an inducible promoter for controlling transcription of the heterologous gene product. Accordingly, delivery of the therapeutic agent in situ is controlled by exposing the cell in situ to conditions, which induce transcription of the heterologous gene.

The mammalian recipient may have a condition that is amenable to gene replacement therapy. As used herein, "gene replacement therapy" refers to administration to the recipient of exogenous genetic material encoding a therapeutic agent and subsequent expression of the administered genetic material in situ. Thus, the phrase "condition amenable to gene replacement therapy" embraces conditions such as genetic diseases (i.e., a disease condition that is attributable to one or more gene defects), acquired pathologies (i.e., a pathological condition which is not attributable to an inborn defect), cancers and prophylactic processes (i.e., prevention of a disease or of an undesired medical condition). Accordingly, as used herein, the term "therapeutic agent" refers to any agent or material, which has a beneficial effect on the mammalian recipient. Thus, "therapeutic agent" embraces both therapeutic and prophylactic molecules having nucleic acid or protein components.

According to one embodiment, the mammalian recipient has a genetic disease and the exogenous genetic material comprises a heterologous gene encoding a therapeutic agent for treating the disease. In yet another embodiment, the mammalian recipient has an acquired pathology and the exogenous genetic material comprises a heterologous gene encoding a therapeutic agent for treating the pathology. According to another embodiment, the patient has a cancer and the exogenous genetic material comprises a heterologous gene encoding an anti-neoplastic agent. In yet another embodiment the patient has an undesired medical condition and the exogenous genetic material comprises a heterologous gene encoding a therapeutic agent for treating the condition.

As used herein, the term "lysosomal enzyme," a "secreted protein," a "nuclear protein," or a "cytoplasmic protein" include variants or biologically active or inactive fragments of these polypeptides. A "variant" of one of the polypeptides is a polypeptide that is not completely identical to a native protein. Such variant protein can be obtained by altering the amino acid sequence by insertion, deletion or substitution of one or more amino acid. The amino acid sequence of the protein is modified, for example by substitution, to create a polypeptide having substantially the same or improved qualities as compared to the native polypeptide. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall peptide retains its spacial conformation but has altered biological activity. For example, common conserved changes might be Asp to Glu, Asn or Gln; His to Lys, Arg or Phe; Asn to Gln, Asp or Glu and Ser to Cys, Thr or Gly. Alanine is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains.

The amino acid changes are achieved by changing the codons of the corresponding nucleic acid sequence. It is known that such polypeptides can be obtained based on substituting certain amino acids for other amino acids in the polypeptide structure in order to modify or improve biological activity. For example, through substitution of alternative amino acids, small conformational changes may be conferred upon a polypeptide that results in increased activity. Alternatively, amino acid substitutions in certain polypeptides may be used to provide residues, which may then be linked to other molecules to provide peptide-molecule conjugates which, retain sufficient properties of the starting polypeptide to be useful for other purposes.

One can use the hydropathic index of amino acids in conferring interactive biological function on a polypeptide, wherein it is found that certain amino acids may be substituted for other amino acids having similar hydropathic indices and still retain a similar biological activity. Alternatively, substitution of like amino acids may be made on the basis of hydrophilicity, particularly where the biological function desired in the polypeptide to be generated in intended for use in immunological embodiments. The greatest local average hydrophilicity of a "protein", as governed by the hydrophilicity of its adjacent amino acids, correlates with its immunogenicity. Accordingly, it is noted that substitutions can be made based on the hydrophilicity assigned to each amino acid.

In using either the hydrophilicity index or hydropathic index, which assigns values to each amino acid, it is preferred to conduct substitutions of amino acids where these values are ±2, with ±1 being particularly preferred, and those with in ±0.5 being the most preferred substitutions.

The variant protein has at least 50%, at least about 80%, or even at least about 90% but less than 100%, contiguous amino acid sequence homology or identity to the amino acid sequence of a corresponding native protein.

The amino acid sequence of the variant polypeptide corresponds essentially to the native polypeptide's amino acid sequence. As used herein "correspond essentially to" refers to a polypeptide sequence that will elicit a biological response substantially the same as the response generated by the native protein. Such a response may be at least 60% of the level generated by the native protein, and may even be at least 80% of the level generated by native protein.

A variant may include amino acid residues not present in the corresponding native protein or deletions relative to the corresponding native protein. A variant may also be a truncated "fragment" as compared to the corresponding native protein, i.e., only a portion of a full-length protein. Protein variants also include peptides having at least one D-amino acid.

The variant protein may be expressed from an isolated DNA sequence encoding the variant protein. "Recombinant" is defined as a peptide or nucleic acid produced by the processes of genetic engineering. It should be noted that it is well-known in the art that, due to the redundancy in the genetic code, individual nucleotides can be readily exchanged in a codon, and still result in an identical amino acid sequence. The terms "protein," "peptide" and "polypeptide" are used interchangeably herein.

The present disclosure provides methods of treating a disease in a mammal by administering an expression vector to a cell or patient. For the gene therapy methods, a person having ordinary skill in the art of molecular biology and gene therapy would be able to determine, without undue experimentation, the appropriate dosages and routes of administration of the expression vector used in the novel methods of the present disclosure.

According to one embodiment, the cells are transformed or otherwise genetically modified in vivo. The cells from the mammalian recipient are transformed (i.e., transduced or transfected) in vivo with a vector containing exogenous genetic material for expressing a heterologous (e.g., recombinant) gene encoding a therapeutic agent and the therapeutic agent is delivered in situ.

As used herein, "exogenous genetic material" refers to a nucleic acid or an oligonucleotide, either natural or synthetic, that is not naturally found in the cells; or if it is naturally found in the cells, it is not transcribed or expressed at biologically significant levels by the cells. Thus, "exogenous genetic material" includes, for example, a non-naturally occurring nucleic acid that can be transcribed into anti-sense RNA, as well as a "heterologous gene" (i.e., a gene encoding a protein which is not expressed or is expressed at biologically insignificant levels in a naturally-occurring cell of the same type).

In the certain embodiments, the mammalian recipient has a condition that is amenable to gene replacement therapy. As used herein, "gene replacement therapy" refers to administration to the recipient of exogenous genetic material encoding a therapeutic agent and subsequent expression of the administered genetic material in situ. Thus, the phrase "condition amenable to gene replacement therapy" embraces conditions such as genetic diseases (i.e., a disease condition that is attributable to one or more gene defects), acquired pathologies (i.e., a pathological condition which is not attributable to an inborn defect), cancers and prophylactic processes (i.e., prevention of a disease or of an undesired medical condition). Accordingly, as used herein, the term "therapeutic agent" refers to any agent or material, which has a beneficial effect on the mammalian recipient. Thus, "therapeutic agent" embraces both therapeutic and prophylactic molecules having nucleic acid (e.g., antisense RNA) and/or protein components.

Alternatively, the condition amenable to gene replacement therapy is a prophylactic process, i.e., a process for preventing disease or an undesired medical condition. Thus, the instant disclosure embraces a cell expression system for delivering a therapeutic agent that has a prophylactic function (i.e., a prophylactic agent) to the mammalian recipient.

In summary, the term "therapeutic agent" includes, but is not limited to, agents associated with the conditions listed above, as well as their functional equivalents. As used herein, the term "functional equivalent" refers to a molecule (e.g., a peptide or protein) that has the same or an improved beneficial effect on the mammalian recipient as the therapeutic agent of which is it deemed a functional equivalent.

The above-disclosed therapeutic agents and conditions amenable to gene replacement therapy are merely illustrative and are not intended to limit the scope of the instant disclosure. The selection of a suitable therapeutic agent for treating a known condition is deemed to be within the scope of one of ordinary skill of the art without undue experimentation.

AAV2 Vectors

In one embodiment, a viral vector of the disclosure is an AAV2 vector. An "AAV2" vector refers to an adeno-associated virus, and may be used to refer to the naturally occurring wild-type virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on capsid protein reactivity with defined antisera, e.g., there are eight known serotypes of primate AAVs, AAV-1 to AAV-8. For example, serotype AAV2 is used to refer to an AAV which contains capsid proteins encoded from the cap gene of AAV2 and a genome containing 5' and 3' ITR sequences from the same AAV2 serotype. As used herein, for example, rAAV1 may be used to refer an AAV having both capsid proteins and 5'-3' ITRs from the same serotype or it may refer to an AAV having capsid proteins from one serotype and 5'-3' ITRs from a different AAV serotype, e.g., capsid from AAV serotype 2 and ITRs from AAV serotype 5. For each example illustrated herein the description of the vector design and production describes the serotype of the capsid and 5'-3' ITR sequences. The abbreviation "rAAV" refers to recombinant adeno-associated virus, also referred to as a recombinant AAV vector (or "rAAV vector").

An "AAV virus" or "AAV viral particle" refers to a viral particle composed of at least one AAV capsid protein (preferably by all of the capsid proteins of a wild-type AAV) and an encapsidated polynucleotide. If the particle comprises heterologous polynucleotide (i.e., a polynucleotide other than a wild-type AAV genome such as a transgene to be delivered to a mammalian cell), it is typically referred to as "rAAV".

In one embodiment, the AAV expression vectors are constructed using known techniques to at least provide as operatively linked components in the direction of transcription, control elements including a transcriptional initiation region, the DNA of interest and a transcriptional termination region. The control elements are selected to be functional in a mammalian cell. The resulting construct which contains the operatively linked components is flanked (5' and 3') with functional AAV ITR sequences.

By "adeno-associated virus inverted terminal repeats" or "AAV ITRs" is meant the art-recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome.

The nucleotide sequences of AAV ITR regions are known. As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV1, AAV2, AAV3, AAV4, AAV5, AAV7, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell.

In one embodiment, AAV ITRs can be derived from any of several AAV serotypes, including without limitation, AAV1, AAV2, AAV3, AAV4, AAV5, AAV7, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

In one embodiment, AAV capsids can be derived from AAV2. Suitable DNA molecules for use in AAV vectors will be less than about 5 kilobases (kb), less than about 4.5 kb, less than about 4 kb, less than about 3.5 kb, less than about 3 kb, less than about 2.5 kb in size and are known in the art.

In one embodiment, the selected nucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, pol II promoters, pol III promoters, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

In one embodiment, both heterologous promoters and other control elements, such as CNS-specific and inducible promoters, enhancers and the like, will be of particular use. Examples of heterologous promoters include the CMV promoter. Examples of CNS-specific promoters include those isolated from the genes from myelin basic protein (MBP), glial fibrillary acid protein (GFAP), and neuron specific enolase (NSE). Examples of inducible promoters include DNA responsive elements for ecdysone, tetracycline, hypoxia and aufin.

In one embodiment, the AAV expression vector which harbors the DNA molecule of interest bounded by AAV ITRs, can be constructed by directly inserting the selected sequence(s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art.

Alternatively, AAV ITRs can be excised from the viral genome or from an AAV vector containing the same and fused 5' and 3' of a selected nucleic acid construct that is present in another vector using standard ligation techniques. For example, ligations can be accomplished in 20 mM Tris-Cl pH 7.5, 10 mM MgCl$_2$, 10 mM DTT, 33 µg/ml BSA, 10 mM-50 mM NaCl, and either 40 uM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 µg/ml total DNA concentrations (5-100 nM total end concentration). AAV vectors which contain ITRs.

Additionally, chimeric genes can be produced synthetically to include AAV ITR sequences arranged 5' and 3' of one or more selected nucleic acid sequences. Preferred codons for expression of the chimeric gene sequence in mammalian CNS cells can be used. The complete chimeric sequence is assembled from overlapping oligonucleotides prepared by standard methods.

In order to produce rAAV virions, an AAV expression vector is introduced into a suitable host cell using known techniques, such as by transfection. A number of transfection techniques are generally known in the art. See, e.g., Sambrook et al. (1989) Molecular Cloning, a laboratory manual, Cold Spring Harbor Laboratories, New York. Particularly suitable transfection methods include calcium phosphate co-precipitation, direct micro-injection into cultured cells, electroporation, liposome mediated gene transfer, lipid-mediated transduction, and nucleic acid delivery using high-velocity microprojectiles.

In one embodiment, suitable host cells for producing rAAV virions include microorganisms, yeast cells, insect cells, and mammalian cells, that can be, or have been, used as recipients of a heterologous DNA molecule. The term includes the progeny of the original cell which has been transfected. Thus, a "host cell" as used herein generally refers to a cell which has been transfected with an exogenous DNA sequence. Cells from the stable human cell line, 293 (readily available through, e.g., the American Type Culture Collection under Accession Number ATCC CRL1573) can be used in the practice of the present disclosure. Particularly, the human cell line 293 is a human embryonic kidney cell line that has been transformed with adenovirus type-5 DNA fragments, and expresses the adenoviral E1a and E1b genes. The 293 cell line is readily transfected, and provides a particularly convenient platform in which to produce rAAV virions.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. Suitable homologues of the AAV rep coding region include the human herpesvirus 6 (HHV-6) rep gene which is also known to mediate AAV-2 DNA replication.

By "AAV cap coding region" is meant the art-recognized region of the AAV genome which encodes the capsid proteins VP1, VP2, and VP3, or functional homologues thereof. These Cap expression products supply the packaging functions which are collectively required for packaging the viral genome.

In one embodiment, AAV helper functions are introduced into the host cell by transfecting the host cell with an AAV helper construct either prior to, or concurrently with, the transfection of the AAV expression vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves. These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. A number of other vectors have been described which encode Rep and/or Cap expression products.

Methods of delivery of viral vectors include injecting the AAV2 into the CSF. Generally, rAAV virions may be introduced into cells of the CNS using either in vivo or in vitro transduction techniques. If transduced in vitro, the desired recipient cell will be removed from the subject, transduced with rAAV virions and reintroduced into the subject. Alternatively, syngeneic or xenogeneic cells can be used where those cells will not generate an inappropriate immune response in the subject.

Suitable methods for the delivery and introduction of transduced cells into a subject have been described. For example, cells can be transduced in vitro by combining recombinant AAV virions with CNS cells e.g., in appropriate media, and screening for those cells harboring the DNA of interest can be screened using conventional techniques such as Southern blots and/or PCR, or by using selectable markers. Transduced cells can then be formulated into pharmaceutical compositions, described more fully below, and the composition introduced into the subject by various techniques, such as by grafting, intramuscular, intravenous, subcutaneous and intraperitoneal injection.

In one embodiment, pharmaceutical compositions will comprise sufficient genetic material to produce a therapeutically effective amount of the nucleic acid of interest, i.e., an amount sufficient to reduce or ameliorate symptoms of the disease state in question or an amount sufficient to confer the desired benefit. The pharmaceutical compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, Tween80, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences (Mack Pub. Co., N.J. 1991).

As is apparent to those skilled in the art in view of the teachings of this specification, an effective amount of viral vector which must be added can be empirically determined. Administration can be effected in one dose, continuously or intermittently throughout the course of treatment. Methods of determining the most effective means and dosages of administration are well known to those of skill in the art and will vary with the viral vector, the composition of the therapy, the target cells, and the subject being treated. Single and multiple administrations can be carried out with the dose level and pattern being selected by the treating physician.

It should be understood that more than one transgene could be expressed by the delivered viral vector. Alternatively, separate vectors, each expressing one or more different transgenes, can also be delivered to the CNS as described herein. Furthermore, it is also intended that the viral vectors delivered by the methods of the present disclosure be combined with other suitable compositions and therapies.

Methods for Introducing Genetic Material into Cells

The exogenous genetic material (e.g., a cDNA encoding one or more therapeutic proteins) is introduced into the cell ex vivo or in vivo by genetic transfer methods, such as transfection or transduction, to provide a genetically modified cell. Various expression vectors (i.e., vehicles for facilitating delivery of exogenous genetic material into a target cell) are known to one of ordinary skill in the art.

As used herein, "transfection of cells" refers to the acquisition by a cell of new genetic material by incorporation of added DNA. Thus, transfection refers to the insertion of nucleic acid into a cell using physical or chemical methods. Several transfection techniques are known to those of ordinary skill in the art including: calcium phosphate DNA co-precipitation; DEAE-dextran; electroporation; cationic liposome-mediated transfection; and tungsten particle-facilitated microparticle bombardment. Strontium phosphate DNA co-precipitation is another possible transfection method.

In contrast, "transduction of cells" refers to the process of transferring nucleic acid into a cell using a DNA or RNA virus. A RNA virus (i.e., a retrovirus) for transferring a nucleic acid into a cell is referred to herein as a transducing chimeric retrovirus. Exogenous genetic material contained within the retrovirus is incorporated into the genome of the transduced cell. A cell that has been transduced with a chimeric DNA virus (e.g., an adenovirus carrying a cDNA encoding a therapeutic agent), will not have the exogenous genetic material incorporated into its genome but will be capable of expressing the exogenous genetic material that is retained extrachromosomally within the cell.

Typically, the exogenous genetic material includes the heterologous gene (usually in the form of a cDNA comprising the exons coding for the therapeutic protein) together with a promoter to control transcription of the new gene. The promoter characteristically has a specific nucleotide sequence necessary to initiate transcription. Optionally, the exogenous genetic material further includes additional sequences (i.e., enhancers) required to obtain the desired gene transcription activity. For the purpose of this discussion an "enhancer" is simply any non-translated DNA sequence which works contiguous with the coding sequence (in cis) to change the basal transcription level dictated by the promoter. The exogenous genetic material may introduced into the cell genome immediately downstream from the promoter so that the promoter and coding sequence are operatively linked so as to permit transcription of the coding sequence. A retroviral expression vector may include an exogenous promoter element to control transcription of the inserted exogenous gene. Such exogenous promoters include both constitutive and inducible promoters.

Naturally-occurring constitutive promoters control the expression of essential cell functions. As a result, a gene under the control of a constitutive promoter is expressed under all conditions of cell growth. Exemplary constitutive promoters include the promoters for the following genes which encode certain constitutive or "housekeeping" functions: hypoxanthine phosphoribosyl transferase (HPRT), dihydrofolate reductase (DHFR), adenosine deaminase, phosphoglycerol kinase (PGK), pyruvate kinase, phosphoglycerol mutase, the actin promoter, and other constitutive promoters known to those of skill in the art. In addition, many viral promoters function constitutively in eucaryotic cells. These include: the early and late promoters of SV40; the long terminal repeats (LTRs) of Moloney Leukemia Virus and other retroviruses; and the thymidine kinase promoter of Herpes Simplex Virus, among many others. Accordingly, any of the above-referenced constitutive promoters can be used to control transcription of a heterologous gene insert.

Genes that are under the control of inducible promoters are expressed only or to a greater degree, in the presence of an inducing agent, (e.g., transcription under control of the metallothionein promoter is greatly increased in presence of certain metal ions). Inducible promoters include responsive elements (REs) which stimulate transcription when their inducing factors are bound. For example, there are REs for serum factors, steroid hormones, retinoic acid and cyclic AMP. Promoters containing a particular RE can be chosen in order to obtain an inducible response and in some cases, the RE itself may be attached to a different promoter, thereby conferring inducibility to the recombinant gene. Thus, by selecting the appropriate promoter (constitutive versus inducible; strong versus weak), it is possible to control both the existence and level of expression of a therapeutic agent in the genetically modified cell. If the gene encoding the therapeutic agent is under the control of an inducible promoter, delivery of the therapeutic agent in situ is triggered by exposing the genetically modified cell in situ to conditions for permitting transcription of the therapeutic agent, e.g., by intraperitoneal injection of specific inducers of the inducible promoters which control transcription of the agent. For example, in situ expression by genetically modified cells of a therapeutic agent encoded by a gene under the control of the metallothionein promoter, is enhanced by contacting the genetically modified cells with a solution containing the appropriate (i.e., inducing) metal ions in situ.

Accordingly, the amount of therapeutic agent that is delivered in situ is regulated by controlling such factors as: (1) the nature of the promoter used to direct transcription of the inserted gene, (i.e., whether the promoter is constitutive or inducible, strong or weak); (2) the number of copies of the exogenous gene that are inserted into the cell; (3) the number of transduced/transfected cells that are administered (e.g., implanted) to the patient; (4) the size of the implant (e.g., graft or encapsulated expression system); (5) the number of implants; (6) the length of time the transduced/transfected cells or implants are left in place; and (7) the production rate of the therapeutic agent by the genetically modified cell. Selection and optimization of these factors for delivery of a therapeutically effective dose of a particular therapeutic agent is deemed to be within the scope of one of ordinary skill in the art without undue experimentation, taking into account the above-disclosed factors and the clinical profile of the patient.

In addition to at least one promoter and at least one heterologous nucleic acid encoding the therapeutic agent, the expression vector may include a selection gene, for example, a neomycin resistance gene, for facilitating selection of cells that have been transfected or transduced with the expression vector. Alternatively, the cells are transfected with two or more expression vectors, at least one vector containing the gene(s) encoding the therapeutic agent(s), the other vector containing a selection gene. The selection of a suitable promoter, enhancer, selection gene and/or signal sequence (described below) is deemed to be within the scope of one of ordinary skill in the art without undue experimentation.

The therapeutic agent can be targeted for delivery to an extracellular, intracellular or membrane location. If it is desirable for the gene product to be secreted from the cells, the expression vector is designed to include an appropriate secretion "signal" sequence for secreting the therapeutic gene product from the cell to the extracellular milieu. If it is desirable for the gene product to be retained within the cell, this secretion signal sequence is omitted. In a similar manner, the expression vector can be constructed to include "retention" signal sequences for anchoring the therapeutic agent within the cell plasma membrane. For example, all membrane proteins have hydrophobic transmembrane regions, which stop translocation of the protein in the membrane and do not allow the protein to be secreted. The construction of an expression vector including signal sequences for targeting a gene product to a particular location is deemed to be within the scope of one of ordinary skill in the art without the need for undue experimentation.

EXAMPLE 1

Treating Central Nervous System Disorders Via Cerebral Spinal Fluid (CSF) in Large Mammals Lysosomal storage disorders (LSDs) constitute a large class of inherited metabolic disorders. Most LSDs are caused by lysosomal enzyme deficiencies which lead to organ damage and often central nervous system (CNS) degeneration. Late infantile neuronal ceroid lipofuscinosis (LINCL) is an autosomal recessive neurodegenerative disease caused by mutations in CLN2, which encodes the lysosomal protease tripeptidyl peptidase 1 (TPP1). LINCL is characterized clinically by progressive motor and cognitive decline, and premature death. Enzyme-replacement therapy (ERT) is currently available for lysosomal storage diseases affecting peripheral tissues, but has not been used in patients with central nervous system (CNS) involvement. A recent study investigated whether enzyme delivery through the cerebrospinal fluid was a potential alternative route to the CNS for LINCL (Chang et al., *Molecular Therapy* 16:649-656, 2008). In this study, the investigators tested if intraventricular delivery of TPP1 to the LINCL mouse was efficacious. They found that infusion of recombinant human TPP1 through an intraventricular cannula led to enzyme distribution in several regions of the brain of treated mice. In vitro activity assays confirmed increased TPP1 activity throughout the rostral-caudal extent of the brain. Treated mice showed attenuated neuropathology, and decreased resting tremor relative to vehicle-treated mice.

The next step was to determine whether long-term, steady-state levels of therapeutic enzymes could be achieved in a mammal. It was discovered that ependymal cells (cells that lie the ventricles in the brain) can be transduced and secrete a targeted enzyme into the cerebral spinal fluid (CSF). It was determined that adeno-associated virus (AAV4) can transduce the ependyma in a mouse model with high efficiency. Davidson et al, *PNAS*, 28:3428-3432, 2000. It was found that in mice there was a normalization of stored substrate levels in disease brain after AAV4 treatment.

In the present work, it was investigated whether global delivery of a vector could be effectively performed in order to achieve steady-state levels of enzyme in the CSF. First, a vector needed to be found that could transduce ependymal cells (cells that line the ventricles) in the brain of larger mammals. Studies were performed in a dog model of LINCL and a non-human primate model of LINCL. The LINCL dogs are normal at birth, but develop neurological signs around 7 months, testable cognitive deficits at ~5-6 months, seizures at 10-11 months, and progressive visual loss.

An adeno-associated virus (AAV) was selected as the vector because of its small size (20 nm), most of its genetic material can be removed ("gutted") so that no viral genes are present, and so that it is replication incompetent. It was previously tested whether adeno-associated virus type 4 (AAV4) vectors could mediate global functional and pathological improvements in a murine model of mucopolysaccharidosis type VII (MPS VII) caused by beta-glucuronidase deficiency (Liu et al., *J. Neuroscience*, 25(41):9321-9327, 2005). Recombinant AAV4 vectors encoding beta-glucuronidase were injected unilaterally into the lateral ventricle of MPS VII mice with established disease. Transduced ependyma expressed high levels of recombinant enzyme, with secreted enzyme penetrating cerebral and cerebellar structures, as well as the brainstem. Immunohistochemical studies revealed close association of recombinant enzyme and brain microvasculature, indicating that beta-glucuronidase reached brain parenchyma via the perivascular spaces lining blood vessels. Aversive associative learning was tested by context fear conditioning. Compared with age-matched heterozygous controls, affected mice showed impaired conditioned fear response and context discrimination. This behavioral deficit was reversed 6 weeks after gene transfer in AAV4 beta-glucuronidase-treated MPS VII mice. The data show that ependymal cells can serve as a source of enzyme secretion into the surrounding brain parenchyma and CSF.

Figure 2:
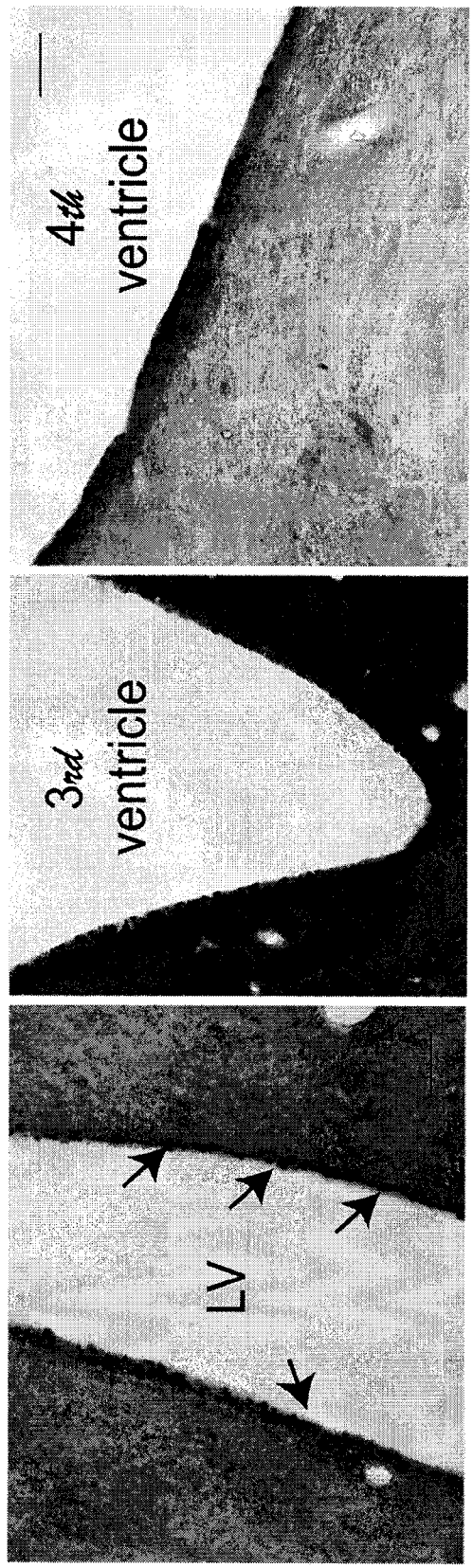
FIG. 2 shows the transfection of AAVeGFP in nonhuman primate brain.
Figure 3:
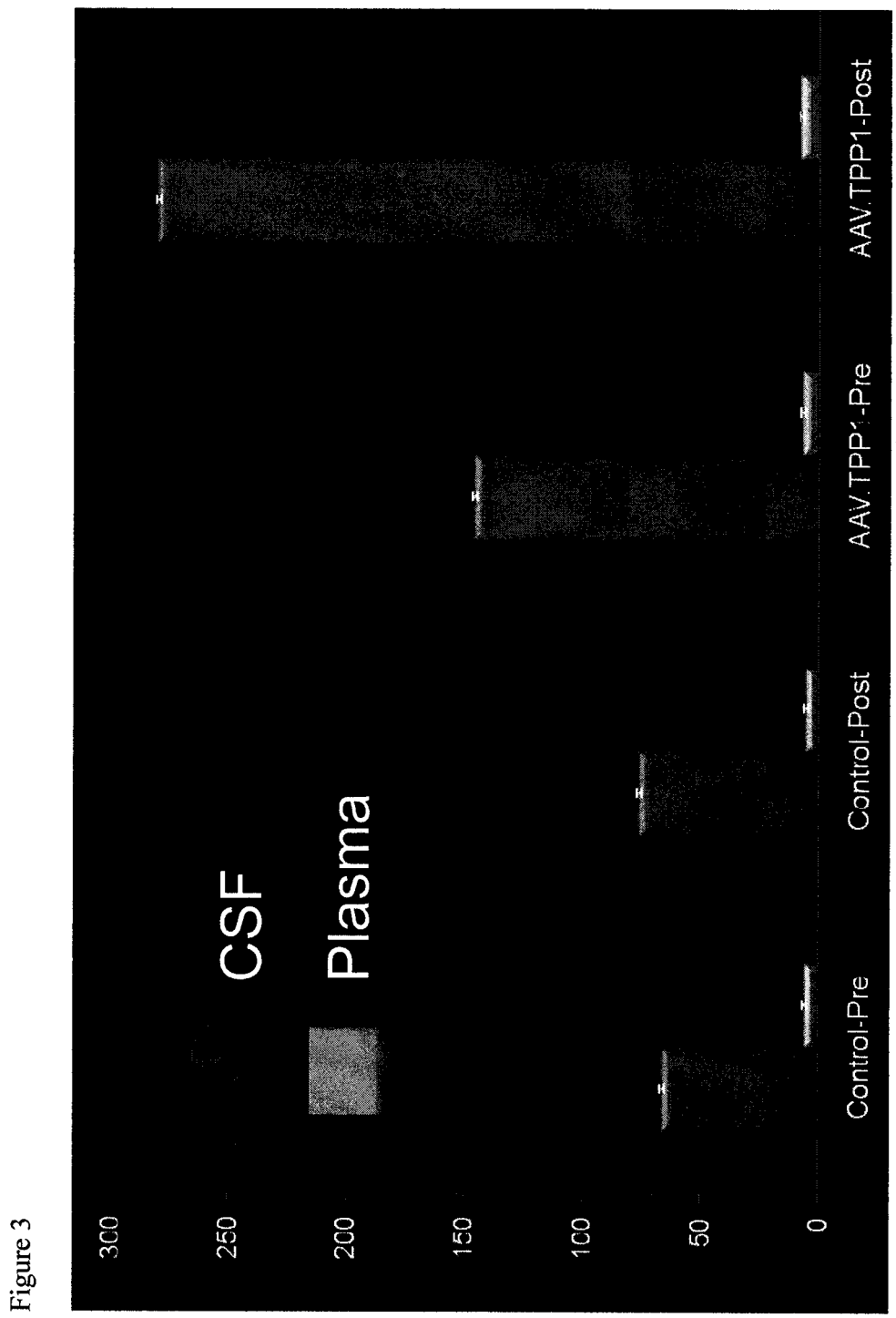
FIG. 3 shows ependymal transduction of TPP1 in NHP brain, indicated significant increase of enzyme in the CSF.
Figure 4:
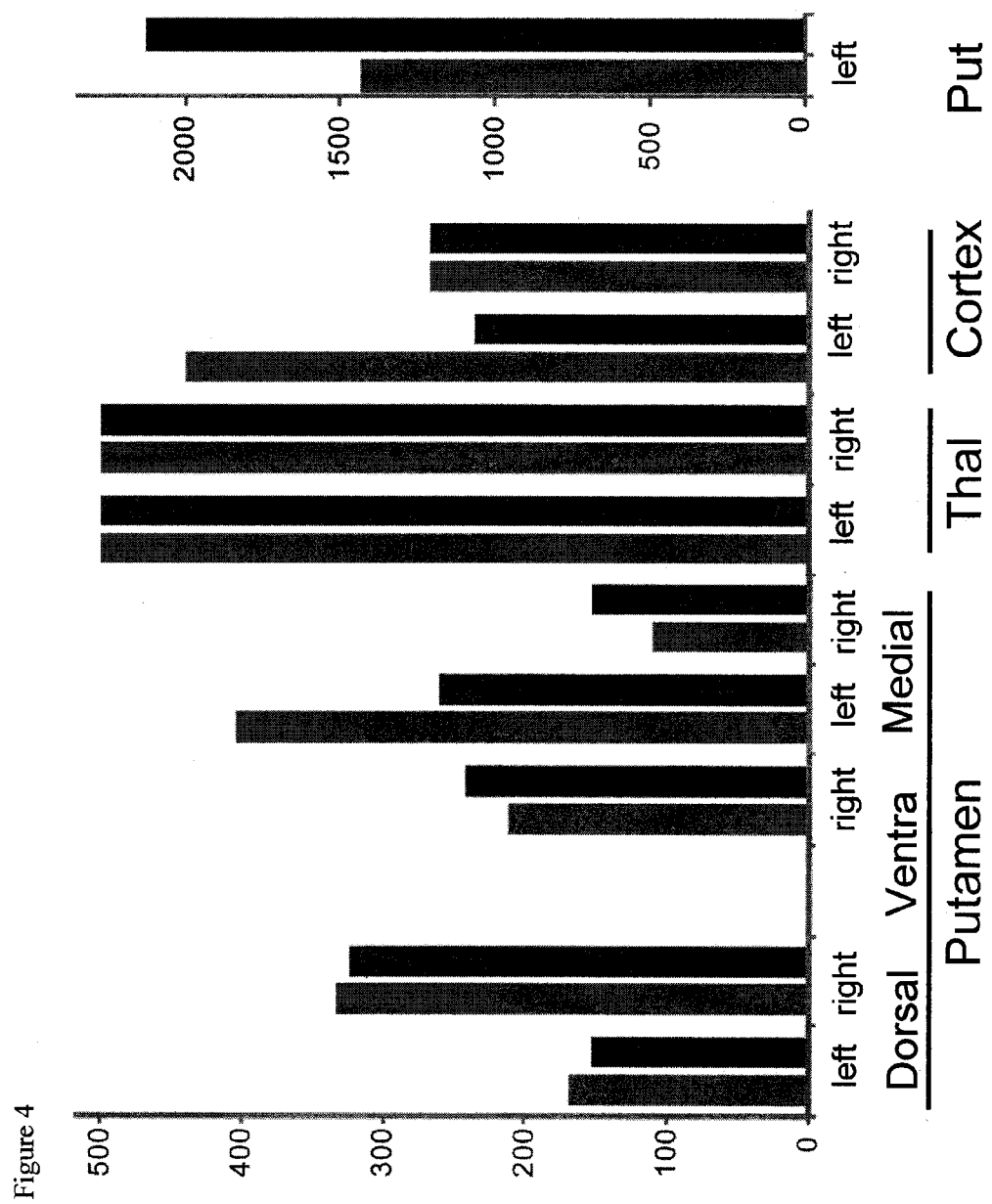
FIG. 4 shows elevated TPP1 activity in various brain regions.

Surprisingly, however, when these studies were extended to large mammals (i.e., dogs and non-human primates), the AAV4 vectors were not effective in targeting the ependyma in these animals. Instead, an AAV2 vector needed to be used. Results of these experiments are shown for dogs (FIG. 1) and nonhuman primates (NHP, FIG. 2). Briefly, rAAV2 was generated encoding TPP1 (AAV2-CLN2), and injected intraventricularly to transduce ependyma (Liu et al., *J. Neuroscience*, 25(41):9321-9327, 2005). TPP1 is the enzyme deficient in LINCL. The data indicated that ependymal transduction in NHP brain resulted in a significant increase of enzyme in CSF (FIG. 3). The results indicated elevated levels of TPP1 activity in various brain regions, where the vertical axis show % control of activity (FIG. 4).

Figure 5:
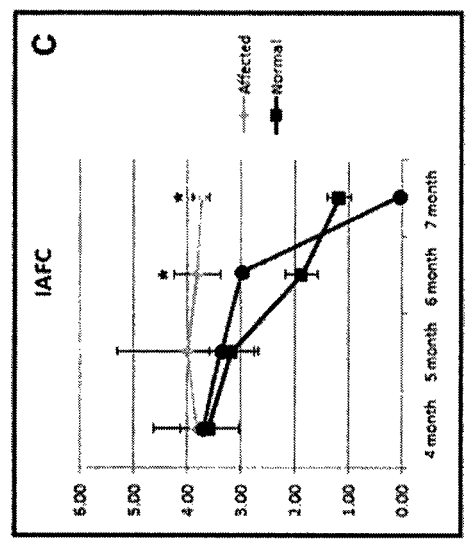
FIG. 5 shows the results of T-maze performance of control and treated dogs. Light circles are for affected dogs; dark squares are for normal dogs, and dark circles are for a TPP–/– dog treated with AAV2-CLN2.

In the first dog that was treated, the delivery of vector was suboptimal, but still exhibited CLN2 activity in the brain. Subsequent dogs underwent ICV delivery with stereotaxy. It was found that the cognitive abilities of the treated dogs were significantly improved over a non-treated dog, as measured by T-maze performance (FIG. 5). Further, the effects of ICV delivery of AAV2-CLN2 in the dog model of LINCL were very pronounced. In the untreated (−/−) animal, large ventricles are present, whereas the brains of the untreated control and the treated animals did not exhibit ventricles. Following delivery of AAV.TPP1 to ventricles of LINCL dogs, detectable enzyme activity was noted in various brain regions, including the cerebellum and upper spinal cord. In two living additional affected dogs, brain atrophy was significantly attenuated, longevity was increased and cognitive function was improved. Finally, in NHP, we show that this method can achieve TPP1 activity levels 2-5 fold above wildtype.

Several AAV vectors were generated and tested to determine the optimal combination of ITR and capsid. Five different combinations were produced, once it was determined that the AAV2 ITR was most effective: AAV2/1 (i.e., AAV2 ITR and AAV1 capsid), AAV2/2, AAV2/4, AAV2/5, and AAV2/8. It was discovered that AAV2/2 worked much better in the large mammals (dogs and NHP), followed by AAV2/8, AAV2/5, AAV2/1 and AAV2/4. This was quite surprising because the order of effectiveness of the viral vectors is the opposite of what was observed in mice.

Thus, the present work has shown that ventricular lining cells can be a source of recombinant enzyme in CSF for distribution throughout the brain, and that AAV2/2 is an effective vehicle for administering therapeutic agents, such as the gene encoding CLN2 (TPP1) in dogs and nonhuman primates.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of treating a central nervous system disease in a non-rodent mammal comprising:
   delivering a therapeutic protein to cerebrospinal fluid (CSF) of the non-rodent mammal by a method comprising,
   (a) intraventricularly administering to the cerebrospinal fluid (CSF) of the non-rodent mammal an rAAV2 particle comprising an AAV2 capsid protein and a vector comprising a nucleic acid encoding the therapeutic protein inserted between a pair of AAV inverted terminal repeats in a manner effective to infect an ependymal cell in the non-rodent mammal, wherein the ependymal cell secretes the therapeutic protein so as to treat the central nervous system disease; or
   (b) intraventricularly administering to ependymal cells of the mammal an rAAV2 particle comprising an AAV2 capsid protein and a vector comprising a nucleic acid encoding the therapeutic protein inserted between a pair of AAV inverted terminal repeats, thereby delivering the nucleic acid to the ependymal cell, wherein the ependymal cell secretes the therapeutic protein so as to treat the central nervous system disease;
   wherein the central nervous system disease is a lysosomal storage disease (LSD) and the therapeutic protein is a lysosomal hydrolase.

2. A method of delivering a lysosomal hydrolase protein to the central nervous system of a non-rodent mammal having a lysosomal storage disease (LSD), comprising intraventricularly administering to the cerebrospinal fluid (CSF) of the non-rodent mammal an rAAV2 particle comprising an AAV2 capsid protein and a vector comprising a nucleic acid encoding the protein lysosomal hydrolase inserted between a pair of AAV inverted terminal repeats in a manner effective to infect ependymal cells in the non-rodent mammal, wherein such that the ependymal cells secrete the protein lysosomal hydrolase into the CSF of the non-rodent mammal and deliver the lysosomal hydrolase to the central nervous system of the mammal.

3. The method of claim 1, wherein the non-rodent mammal is a primate or dog.

4. The method of claim 3, wherein the non-rodent mammal is a primate.

5. The method of claim 3, wherein the non-rodent mammal is a dog.

6. The method of claim 1 or 2, wherein the protein LSD is late infantile ceroid lipofuscinoses (LINCL) and the lysosomal hydrolase is tripeptidyl peptidase 1 (TPP1).

7. The method of claim 1, wherein the non-rodent mammal is human.

8. The method of claim 1 or 2, wherein the LSD is infantile or late infantile ceroid lipofuscinoses (LINCL), neuronopathic Gaucher, Juvenile Batten, Fabry, MLD, Sanfilippo A, Hunter, Krabbe, Morquio, Pompe, Niemann-Pick C, Tay-Sachs, Hurler (MPS-I H), Sanfilippo B, Maroteaux-Lamy, Niemann-Pick A, Cystinosis, Hurler-Scheie (MPS-I H/S), Sly Syndrome (MPS VII), Scheie (MPS-I S), Infantile Batten, GM1 Gangliosidosis, Mucolipidosis type II/III, or Sandhoff disease.

9. The method of claim 8, wherein the LSD is late infantile ceroid lipofuscinoses (LINCL).

10. The method of claim 8, wherein the LSD is Juvenile Batten or Infantile Batten disease.

11. The method of claim 1, wherein at least one of the pair of AAV inverted terminal repeats is an AAV2 ITR.

12. The method of claim 2, wherein at least one of the pair of AAV inverted terminal repeats is an AAV2 ITR.

13. The method of claim 1, wherein the ependymal cells provide a source of secreted protein that is distributed to or penetrates the cerebral or cerebellar structures of the non-rodent mammal.

14. The method of claim 1, wherein the ependymal cells provide a source of secreted protein that is distributed to or penetrates the upper spinal cord or brainstem of the non-rodent mammal.

15. The method of claim 1, wherein the ependymal cells provide a source of secreted protein that is distributed throughout the brain of the non-rodent mammal.

16. The method of claim 10, wherein the lysosomal hydrolase is TPP1 and the non-rodent mammal is a human.

17. The method of claim 2, wherein the non-rodent mammal is a primate or dog.

18. The method of claim 17, wherein the non-rodent mammal is a primate.

19. The method of claim 18, wherein the primate is human.

20. The method of claim 2, wherein the non-rodent mammal is a dog.

21. The method of claim 2, wherein the lysosomal hydrolase is TPP1.

22. The method of claim 2, wherein the ependymal cells provide a source of secreted protein that is distributed to or penetrates the cerebral or cerebellar structures of the non-rodent mammal.

23. The method of claim 2, wherein the ependymal cells provide a source of secreted protein that is distributed to or penetrates the upper spinal cord or brainstem of the non-rodent mammal.

24. The method of claim 2, wherein the ependymal cells provide a source of secreted protein that is distributed throughout the brain of the non-rodent mammal.

* * * * *

SEQUENCE LISTING

```
<160> NUMBER OF SEQ ID NOS: 4

<210> SEQ ID NO 1
<211> LENGTH: 735
<212> TYPE: PRT
<213> ORGANISM: Adeno-associated virus 2

<400> SEQUENCE: 1

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175
```

-continued

```
Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590
```

-continued

```
Ala Asp Val Asn Thr Gln Gly Val Leu Pro Gly Met Val Trp Gln Asp
             595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
                660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
            690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 2
<211> LENGTH: 734
<212> TYPE: PRT
<213> ORGANISM: Adeno-associated virus 4

<400> SEQUENCE: 2

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
                20                  25                  30

Ala Asn Gln Gln His Gln Asp Asn Ala Arg Gly Leu Val Leu Pro Gly
            35                  40                  45

Tyr Lys Tyr Leu Gly Pro Gly Asn Gly Leu Asp Lys Gly Glu Pro Val
        50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Gln Arg Leu Gln Gly Asp Thr Ser Phe Gly Gly Asn
            100                 105                 110

Leu Gly Arg Ala Val Phe Gln Ala Lys Lys Arg Val Leu Glu Pro Leu
        115                 120                 125

Gly Leu Val Glu Gln Ala Gly Glu Thr Ala Pro Gly Lys Lys Arg Pro
    130                 135                 140

Leu Ile Glu Ser Pro Gln Gln Pro Asp Ser Ser Thr Gly Ile Gly Lys
145                 150                 155                 160

Lys Gly Lys Gln Pro Ala Lys Lys Lys Leu Val Phe Glu Asp Glu Thr
                165                 170                 175

Gly Ala Gly Asp Gly Pro Pro Glu Gly Ser Thr Ser Gly Ala Met Ser
            180                 185                 190

Asp Asp Ser Glu Met Arg Ala Ala Ala Gly Gly Ala Val Glu Gly Gly
        195                 200                 205

Gly Gln Gly Ala Asp Gly Val Gly Asn Ala Ser Gly Asp Trp His Cys
    210                 215                 220

Asp Ser Thr Trp Ser Glu Gly His Val Thr Thr Thr Ser Thr Arg Thr
225                 230                 235                 240
```

```
Trp Val Leu Pro Thr Tyr Asn Asn His Leu Tyr Lys Arg Leu Gly Glu
            245                 250                 255

Ser Leu Gln Ser Asn Thr Tyr Asn Gly Phe Ser Thr Pro Trp Gly Tyr
        260                 265                 270

Phe Asp Phe Asn Arg Phe His Cys His Phe Ser Pro Arg Asp Trp Gln
        275                 280                 285

Arg Leu Ile Asn Asn Asn Trp Gly Met Arg Pro Lys Ala Met Arg Val
        290                 295                 300

Lys Ile Phe Asn Ile Gln Val Lys Glu Val Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Leu Val Thr Gly Asn Thr Ser Gln Gln Thr Asp Arg Asn
        370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
                405                 410                 415

Met Tyr Ala His Ser Gln Ser Leu Asp Arg Leu Met Asn Pro Leu Ile
            420                 425                 430

Asp Gln Tyr Leu Trp Gly Leu Gln Ser Thr Thr Thr Gly Thr Thr Leu
        435                 440                 445

Asn Ala Gly Thr Ala Thr Thr Asn Phe Thr Lys Leu Arg Pro Thr Asn
450                 455                 460

Phe Ser Asn Phe Lys Lys Asn Trp Leu Pro Gly Pro Ser Ile Lys Gln
465                 470                 475                 480

Gln Gly Phe Ser Lys Thr Ala Asn Gln Asn Tyr Lys Ile Pro Ala Thr
                485                 490                 495

Gly Ser Asp Ser Leu Ile Lys Tyr Glu Thr His Ser Thr Leu Asp Gly
            500                 505                 510

Arg Trp Ser Ala Leu Thr Pro Gly Pro Pro Met Ala Thr Ala Gly Pro
        515                 520                 525

Ala Asp Ser Lys Phe Ser Asn Ser Gln Leu Ile Phe Ala Gly Pro Lys
        530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
                565                 570                 575

Asn Leu Pro Gly Gly Asp Gln Ser Asn Ser Asn Leu Pro Thr Val Asp
            580                 585                 590

Arg Leu Thr Ala Leu Gly Ala Val Pro Gly Met Val Trp Gln Asn Arg
        595                 600                 605

Asp Ile Tyr Tyr Gln Gly Pro Ile Trp Ala Lys Ile Pro His Thr Asp
        610                 615                 620

Gly His Phe His Pro Ser Pro Leu Ile Gly Gly Phe Gly Leu Lys His
625                 630                 635                 640

Pro Pro Pro Gln Ile Phe Ile Lys Asn Thr Pro Val Pro Ala Asn Pro
                645                 650                 655
```

```
Ala Thr Thr Phe Ser Ser Pro Val Asn Ser Phe Ile Thr Gln Tyr
                660                 665                 670

Ser Thr Gly Gln Val Ser Val Gln Ile Asp Trp Glu Ile Gln Lys Glu
        675                 680                 685

Arg Ser Lys Arg Trp Asn Pro Glu Val Gln Phe Thr Ser Asn Tyr Gly
        690                 695                 700

Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His His Leu
                725                 730

<210> SEQ ID NO 3
<211> LENGTH: 2208
<212> TYPE: DNA
<213> ORGANISM: Adeno-associated virus 2

<400> SEQUENCE: 3
atggctgccg atggttatct tccagattgg ctcgaggaca ctctctctga aggaataaga      60
cagtggtgga agctcaaacc tggcccacca ccaccaaagc ccgcagagcg cataaggac     120 gacagcaggg gtcttgtgct tcctgggtac aagtacctcg gacccttcaa cggactcgac    180
aagggagagc cggtcaacga ggcagacgcc gcggccctcg agcacgacaa agcctacgac    240
cggcagctcg acagcggaga caacccgtac ctcaagtaca accacgccga cgcggagttt    300
caggagcgcc ttaaagaaga tacgtctttt gggggcaacc tcggacgagc agtcttccag    360
gcgaaaaaga gggttcttga acctctgggc ctggttgagg aacctgttaa gacggctccg    420
ggaaaaaaga ggccggtaga gcactctcct gtggagccag actcctcctc gggaaccgga    480
aaggcgggcc agcagcctgc aagaaaaaga ttgaattttg gtcagactgg agacgcagac    540
tcagtacctg accccagcc tctcggacag ccaccagcag cccctctgg tctgggaact    600 aatacgatgg ctacaggcag tggcgcacca atggcagaca taacgagggg cgccgacgga    660
gtgggtaatt cctcgggaaa ttggcattgc gattccacat ggatgggcga cagagtcatc    720
accaccagca cccgaacctg ggccctgccc acctacaaca accacctcta caaacaaatt    780
tccagccaat caggagcctc gaacgacaat cactactttg gctacagcac ccttggggg    840 tattttgact tcaacagatt ccactgccac ttttcaccac gtgactggca agactcatc    900 aacaacaact ggggattccg acccaagaga ctcaacttca agctctttaa cattcaagtc    960
aaagaggtca cgcagaatga cggtacgacg acgattgcca ataaccttac cagcacggtt   1020
caggtgttta ctgactcgga gtaccagctc ccgtacgtcc tcggctcggc gcatcaagga   1080
tgcctcccgc cgttcccagc agacgtcttc atggtgccac agtatggata cctcaccctg   1140
aacaacggga gtcaggcagt aggacgctct tcattttact gcctggagta ctttccttct   1200
cagatgctgc gtaccggaaa caactttacc ttcagctaca cttttgagga cgttcctttc   1260
cacagcagct acgctcacag ccagagtctg gaccgtctca tgaatcctct catcgaccag   1320
tacctgtatt acttgagcag aacaaacact ccaagtggaa ccaccacgca gtcaaggctt   1380
cagttttctc aggccggagc gagtgacatt cgggaccagt ctaggaactg gcttcctgga   1440
ccctgttacc gccagcagcg agtatcaaag acatctgcgg ataacaacaa cagtgaatac   1500
tcgtggactg gagctaccaa gtaccacctc aatggcagag actctctggt gaatccgggc   1560
ccggccatgg caagccacaa ggacgatgaa gaaaagtttt tccctcagag cggggttctc   1620
atctttggga agcaaggctc agagaaaaca aatgtggaca ttgaaaaggt catgattaca   1680
```

```
gacgaagagg aaatcaggac aaccaatccc gtggctacgg agcagtatgg ttctgtatct   1740
accaacctcc agagaggcaa cagacaagca gctaccgcag atgtcaacac acaaggcgtt   1800
cttccaggca tggtctggca ggacagagat gtgtaccttc aggggcccat ctgggcaaag   1860
attccacaca cggacggaca ttttcacccc tctcccctca tgggtggatt cggacttaaa   1920
caccctcctc cacagattct catcaagaac accccggtac ctgcgaatcc ttcgaccacc   1980
ttcagtgcgg caaagtttgc ttccttcatc acacagtact ccacgggaca ggtcagcgtg   2040
gagatcgagt gggagctgca gaaggaaaac agcaaacgct ggaatcccga aattcagtac   2100
acttccaact acaacaagtc tgttaatgtg gactttactg tggacactaa tggcgtgtat   2160
tcagagcctc gccccattgg caccagatac ctgactcgta atctgtaa            2208

<210> SEQ ID NO 4
<211> LENGTH: 2205
<212> TYPE: DNA
<213> ORGANISM: Adeno-associated virus 4

<400> SEQUENCE: 4
atgactgacg gttaccttcc agattggcta gaggacaacc tctctgaagg cgttcgagag     60
tggtgggcgc tgcaacctgg agcccctaaa cccaaggcaa atcaacaaca tcaggacaac    120
gctcggggtc ttgtgcttcc gggttacaaa tacctcggac ccggcaacgg actcgacaag    180
ggggaacccg tcaacgcagc ggacgcggca gccctcgagc acgacaaggc ctacgaccag    240
cagctcaagg ccggtgacaa cccctacctc aagtacaacc acgccgacgc ggagttccag    300
cagcggcttc agggcgacac atcgtttggg ggcaacctcg gcagagcagt cttccaggcc    360
aaaaagaggg ttcttgaacc tcttggtctg gttgagcaag cgggtgagac ggctcctgga    420
aagaagagac cgttgattga atcccccag cagcccgact cctccacggg tatcggcaaa    480
aaaggcaagc agccggctaa aaagaagctc gttttcgaag acgaaactgg agcaggcgac    540
ggaccccctg agggatcaac ttccggagcc atgtctgatg acagtgagat gcgtgcagca    600
gctggcggag ctgcagtcga gggcggacaa ggtgccgatg gagtgggtaa tgcctcgggt    660
gattggcatt gcgattccac ctggtctgag ggccacgtca cgaccaccag caccagaacc    720
tgggtcttgc ccacctacaa caaccacctc tacaagcgac tcggagagag cctgcagtcc    780
aacacctaca cggattctc cacccctgg ggatactttg acttcaaccg cttccactgc    840
cacttctcac acgtgactg gcagcgactc atcaacaaca ctggggcat gcgacccaaa    900 gccatgcggg tcaaaatctt caacatccag gtcaaggagg tcacgacgtc gaacggcgag    960
acaacggtgg ctaataacct taccagcacg gttcagatct ttgcggactc gtcgtacgaa   1020
ctgccgtacg tgatggatgc gggtcaagag ggcagcctgc ctcctttccc aacgacgtc   1080 tttatggtgc cccagtacgg ctactgtgga ctggtgaccg gcaacacttc gcagcaacag   1140
actgacagaa atgccttcta ctgcctggag tactttcctt cgcagatgct gcggactggc   1200 aacaacttg aaattacgta cagttttgag aaggtgcctt ccactcgat gtacgcgcac   1260 agccagagcc tggaccggct gatgaaccct ctcatcgacc agtacctgtg gggactgcaa   1320
tcgaccacca ccgaaccac cctgaatgcc gggactgcca ccaactt taccaagctg   1380 cggcctacca acttttccaa cttttaaaaag aactggctgc ccgggccttc aatcaagcag   1440
cagggcttct caaagactgc caatcaaaac tacaagatcc ctgccaccgg gtcagacagt   1500
ctcatcaaat acgagacgca cagcactctg gacggaagat ggagtgccct gacccccgga   1560
cctccaatgg ccacggctgg acctgcggac agcaagttca gcaacagcca gctcatcttt   1620
```

```
gcggggccta aacagaacgg caacacggcc accgtacccg ggactctgat cttcacctct    1680
gaggaggagc tggcagccac caacgccacc gatacggaca tgtggggcaa cctacctggc    1740
ggtgaccaga gcaacagcaa cctgccgacc gtggacagac tgacagcctt gggagccgtg    1800
cctggaatgg tctggcaaaa cagagacatt tactaccagg gtcccatttg ggccaagatt    1860
cctcataccg atggacactt tcacccctca ccgctgattg gtgggtttgg gctgaaacac    1920
ccgcctcctc aaatttttat caagaacacc ccggtacctg cgaatcctgc aacgaccttc    1980
agctctactc cggtaaactc cttcattact cagtacagca ctggccaggt gtcggtgcag    2040
attgactggg agatccagaa ggagcggtcc aaacgctgga accccgaggt ccagtttacc    2100
tccaactacg gacagcaaaa ctctctgttg tgggctcccg atgcggctgg gaaatacact    2160
gagcctaggg ctatcggtac ccgctacctc acccaccacc tgtaa                   2205
```